(12) United States Patent
Scott et al.

(10) Patent No.: US 7,557,129 B2
(45) Date of Patent: Jul. 7, 2009

(54) CYANOPYRIDINE DERIVATIVES USEFUL IN THE TREATMENT OF CANCER AND OTHER DISORDERS

(75) Inventors: William J. Scott, Guilford, CT (US); Jacques Dumas, Bethany, CT (US); Stephen Boyer, Hilden (DE); Wendy Lee, Hamden, CT (US); Yuanwei Chen, North Haven, CT (US); Barton Phillips, New Haven, CT (US); Sharad Verma, New Haven, CT (US); Jianqing Chen, New Haven, CT (US); Zhi Chen, Hamden, CT (US); Jianmei Fan, Hamden, CT (US); Brian Raudenbush, Charlton, MA (US); Aniko Redman, Derby, CT (US); Lin Yi, Milford, CT (US); Qingming Zhu, West Haven, CT (US); Lila Adnane, Madison, CT (US)

(73) Assignee: Bayer Healthcare LLC, Tarrytown, NY (US)

( * ) Notice: Subject to any disclaimer, the term of this patent is extended or adjusted under 35 U.S.C. 154(b) by 329 days.

(21) Appl. No.: 10/788,029

(22) Filed: Feb. 27, 2004

(65) Prior Publication Data

US 2004/0235829 A1 Nov. 25, 2004

Related U.S. Application Data

(60) Provisional application No. 60/450,323, filed on Feb. 28, 2003, provisional application No. 60/450,324, filed on Feb. 28, 2003, provisional application No. 60/450,348, filed on Feb. 28, 2003.

(51) Int. Cl.
*A61K 31/4433* (2006.01)
*C07D 405/12* (2006.01)

(52) U.S. Cl. .................. 514/338; 546/283.7

(58) Field of Classification Search .............. 546/283.7; 514/338
See application file for complete search history.

(56) References Cited

U.S. PATENT DOCUMENTS

| 5,861,419 | A | 1/1999 | Dube et al. |
| 6,242,601 | B1 | 6/2001 | Breu et al. |
| 2005/0059703 | A1* | 3/2005 | Wilhelm et al. .............. 514/338 |

FOREIGN PATENT DOCUMENTS

| WO | 99/32106 | A | 7/1999 |
| WO | 00/41698 | A | 7/2000 |
| WO | 00/43384 | A | 7/2000 |
| WO | 01/36403 | A | 5/2001 |
| WO | 01/57008 | A | 8/2001 |
| WO | 02/062763 | A | 8/2002 |
| WO | 02/083628 | A | 10/2002 |
| WO | 02/085859 | A | 10/2002 |
| WO | 03/099771 | A | 12/2003 |

OTHER PUBLICATIONS

Dumas J: "Protein Kinase Inhibitors From the Urea Class", Current Opinion in Drug Discovery and Development, Current Drugs, London, GB, vol. 5, No. 5, 2002, pp. 718-727.
EP Search Report Dated Oct. 14, 2004, 6 Pages.
International Search Report dated Sep. 24, 2004, 6 pages.

* cited by examiner

*Primary Examiner*—Patricia L Morris
(74) *Attorney, Agent, or Firm*—Jessica Monachello

(57) ABSTRACT

This invention relates to novel diaryl ureas, pharmaceutical compositions containing such compounds and the use of those compounds or compositions for treating hyper-proliferative and angiogenesis disorders, as a sole agent or in combination with cytotoxic therapies.

18 Claims, No Drawings

CYANOPYRIDINE DERIVATIVES USEFUL IN THE TREATMENT OF CANCER AND OTHER DISORDERS

RELATED APPLICATIONS

This application claims priority to Ser. No. 60/450,323, filed Feb. 28, 2003, Ser. No. 60/450,324 filed Feb. 28, 2003 and Ser. No. 60/450,348 filed Feb. 28, 2003 which are incorporated by reference herein.

FIELD OF THE INVENTION

This invention relates to novel compounds, pharmaceutical compositions containing such compounds and the use of these compounds or compositions for treating hyper-proliferative and angiogenesis disorders, as a sole agent or in combination with other active ingredients, e.g., cytotoxic therapies.

BACKGROUND OF THE INVENTION

Activation of the ras signal transduction pathway indicates a cascade of events that have a profound impact on cellular proliferation, differentiation, and transformation. Raf kinase, a downstream effector of ras, is recognized as a key mediator of these signals from cell surface receptors to the cell nucleus (Lowy, D. R.; Willumsen, B. M. *Ann. Rev. Biochem.* 1993, 62, 851; Bos, J. L. *Cancer Res.* 1989, 49, 4682). It has been shown that inhibiting the effect of active ras by inhibiting the raf kinase signaling pathway by administration of deactivating antibodies to raf kinase or by co-expression of dominant negative raf kinase or dominant negative MEK, the substrate of raf kinase, leads to the reversion of transformed cells to the normal growth phenotype (see: Daum et al. *Trends Biochem. Sci.* 1994, 19, 474-80; Fridman et al. *J. Biol. Chem.* 1994, 269, 30105-8. Kolch et al. (*Nature* 1991, 349, 426-28) have further indicated that inhibition of raf expression by antisense RNA blocks cell proliferation in membrane-associated oncogenes. Similarly, inhibition of raf kinase (by antisense oligodeoxynucleotides) has been correlated in vitro and in vivo with inhibition of the growth of a variety of human tumor types (Monia et al., *Nat. Med.* 1996, 2, 668-75). Some examples of small molecule inhibitors of Raf kinase activity are important agents for the treatment of cancer. (Naumann, U.; Eisenmann-Tappe, I.; Rapp, U. R. *Recent Results Cancer Res.* 1997, 143, 237; Monia, B. P.; Johnston, J. F.; Geiger, T.; Muller, M.; Fabbro, D. *Nature Medicine* 1996, 2, 668).

To support progressive tumor growth beyond the size of 1-2 mm$^3$, it is recognized that tumor cells require a functional stroma, a support structure consisting of fibroblast, smooth muscle cells, endothelial cells, extracellular matrix proteins, and soluble factors (Folkman, J., *Semin Oncol,* 2002. 29(6 Suppl 16), 15-8). Tumors induce the formation of stromal tissues through the secretion of soluble growth factors such as PDGF and transforming growth factor-beta (TGF-beta), which in turn stimulate the secretion of complimentary factors by host cells such as fibroblast growth factor (FGF), epidermal growth factor (EGF), and vascular endothelial growth factor (VEGF). These stimulatory factors induce the formation of new blood vessels, or angiogenesis, which brings oxygen and nutrients to the tumor and allows it to grow and provides a route for metastasis. It is believed some therapies directed at inhibiting stroma formation will inhibit the growth of epithelial tumors from a wide variety of histological types. (George, D. *Semin Oncol,* 2001. 28(5 Suppl 17), 27-33; Shaheen, R. M., et al., *Cancer Res,* 2001. 61(4), 1464-8; Shaheen, R. M., et al. *Cancer Res,* 1999. 59(21), 5412-6). However, because of the complex nature and the multiple growth factors involved in angiogenesis process and tumor progression, an agent targeting a single pathway may have limited efficacy. It is desirable to provide treatment against a number of key signaling pathways utilized by tumors to induce angiogenesis in the host stroma. These include PDGF, a potent stimulator of stroma formation (Ostman, A. and C. H. Heldin, *Adv Cancer Res,* 2001, 80, 1-38), FGF, a chemoattractant and mitogen for fibroblasts and endothelial cells, and VEGF, a potent regulator of vascularization.

PDGF is another key regulator of stromal formation which is secreted by many tumors in a paracrine fashion and is believed to promote the growth of fibroblasts, smooth muscle and endothelial cells, promoting stroma formation and angiogenesis. PDGF was originally identified as the v-sis oncogene product of the simian sarcoma virus (Heldin, C. H., et al., *J Cell Sci Suppl,* 1985, 3, 65-76). The growth factor is made up of two peptide chains, referred to as A or B chains which share 60% homology in their primary amino acid sequence. The chains are disulfide cross linked to form the 30 kDa mature protein composed of either M, BB or AB homo- or heterodimers. PDGF is found at high levels in platelets, and is expressed by endothelial cells and vascular smooth muscle cells. In addition, the production of PDGF is up regulated under low oxygen conditions such as those found in poorly vascularized tumor tissue (Kourembanas, S., et al., *Kidney Int,* 1997, 51(2), 438-43). PDGF binds with high affinity to the PDGF receptor, a 1106 amino acid 124 kDa transmembrane tyrosine kinase receptor (Heldin, C. H., A. Ostman, and L. Ronnstrand, *Biochim Biophys Acta,* 1998. 1378(1), 79-113). PDGFR is found as homo- or heterodimer chains which have 30% homology overall in their amino acid sequence and 64% homology between their kinase domains (Heldin, C. H., et al. *Embo J,* 1988, 7(5), 1387-93). PDGFR is a member of a family of tyrosine kinase receptors with split kinase domains that includes VEGFR2 (KDR), VEGFR3 (Flt4), c-Kit, and FLT3. The PDGF receptor is expressed primarily on fibroblast, smooth muscle cells, and pericytes and to a lesser extent on neurons, kidney mesangial, Leydig, and Schwann cells of the central nervous system. Upon binding to the receptor, PDGF induces receptor dimerization and undergoes auto- and trans-phosphorylation of tyrosine residues which increase the receptors' kinase activity and promotes the recruitment of downstream effectors through the activation of SH2 protein binding domains. A number of signaling molecules form complexes with activated PDGFR including PI-3-kinase, phospholipase C-gamma, src and GAP (GTPase activating protein for p21-ras) (Soskic, V., et al. *Biochemistry,* 1999, 38(6), 1757-64). Through the activation of PI-3-kinase, PDGF activates the Rho signaling pathway inducing cell motility and migration, and through the activation of GAP, induces mitogenesis through the activation of p21-ras and the MAPK signaling pathway.

In adults, it is believed the major function of PDGF is to facilitate and increase the rate of wound healing and to maintain blood vessel homeostasis (Baker, E. A. and D. J. Leaper, *Wound Repair Regen,* 2000. 8(5), 392-8; Yu, J., A. Moon, and H. R. Kim, *Biochem Biophys Res Commun,* 2001. 282(3), 697-700). PDGF is found at high concentrations in platelets and is a potent chemoattractant for fibroblast, smooth muscle cells, neutrophils and macrophages. In addition to its role in wound healing PDGF is known to help maintain vascular homeostasis. During the development of new blood vessels, PDGF recruits pericytes and smooth muscle cells that are needed for the structural integrity of the vessels. PDGF is thought to play a similar role during tumor neovascularization. As part of its role in angiogenesis PDGF controls interstitial fluid pressure, regulating the permeability of vessels through its regulation of the interaction between connective tissue cells and the extracellular matrix. Inhibiting PDGFR activity can lower interstitial pressure and facilitate the influx of cytotoxics into tumors improving the anti-tumor efficacy of these agents (Pietras, K., et al. *Cancer Res,* 2002. 62(19), 5476-84; Pietras, K., et al. *Cancer Res,* 2001. 61 (7), 2929-34).

PDGF can promote tumor growth through either the paracrine or autocrine stimulation of PDGFR receptors on stromal cells or tumor cells directly, or through the amplification of the receptor or activation of the receptor by recombination. Over expressed PDGF can transform human melanoma cells and keratinocytes (Forsberg, K., et al. *Proc Natl Acad Sci USA.,* 1993. 90(2), 393-7; Skobe, M. and N. E. Fusenig, *Proc Natl Acad Sci USA,* 1998. 95(3), 1050-5), two cell types that do not express PDGF receptors, presumably by the direct effect of PDGF on stroma formation and induction of angiogenesis. This paracrine stimulation of tumor stroma is also observed in carcinomas of the colon, lung, breast, and prostate (Bhardwaj, B., et al. *Clin Cancer Res,* 1996, 2(4), 773-82; Nakanishi, K., et al. *Mod Pathol,* 1997, 10(4), 341-7; Sundberg, C., et al. *Am J Pathol,* 1997, 151(2), 479-92; Lindmark, G., et al. *Lab Invest,* 1993, 69(6), 682-9; Vignaud, J. M., et al, *Cancer Res,* 1994, 54(20), 5455-63) where the tumors express PDGF, but not the receptor. The autocrine stimulation of tumor cell growth, where a large faction of tumors analyzed express both the ligand PDGF and the receptor, has been reported in glioblastomas (Fleming, T. P., et al. *Cancer Res,* 1992, 52(16), 4550-3), soft tissue sarcomas (Wang, J., M. D. Coltrera, and A. M. Gown, *Cancer Res,* 1994, 54(2), 560-4) and cancers of the ovary (Henriksen, R., et al. *Cancer Res,* 1993, 53(19), 4550-4), prostate (Fudge, K., C. Y. Wang, and M. E. Stearns, *Mod Pathol,* 1994, 7(5), 549-54), pancreas (Funa, K., et al. *Cancer Res,* 1990, 50(3), 748-53) and lung (Antoniades, H. N., et al., *Proc Natl Acad Sci USA,* 1992, 89(9), 3942-6). Ligand independent activation of the receptor is found to a lesser extent but has been reported in chronic myelomonocytic leukemia (CMML) where the a chromosomal translocation event forms a fusion protein between the Ets-like transcription factor TEL and the PDGF receptor. In addition, activating mutations in PDGFR have been found in gastrointestinal stromal tumors in which c-Kit activation is not involved (Heinrich, M. C., et al., *Science,* 2003, 9, 9).

Certain PDGFR inhibitors will interfere with tumor stromal development and are believed to inhibit tumor growth and metastasis.

Another major regulator of angiogenesis and vasculogenesis in both embryonic development and some angiogenic-dependent diseases is vascular endothelial growth factor (VEGF; also called vascular permeability factor, VPF). VEGF represents a family of isoforms of mitogens existing in homodimeric forms due to alternative RNA splicing. The VEGF isoforms are reported to be highly specific for vascular endothelial cells (for reviews, see: Farrara et al. *Endocr. Rev.* 1992, 13, 18; Neufield et al. *FASEB J.* 1999, 13, 9).

VEGF expression is reported to be induced by hypoxia (Shweiki et al. *Nature* 1992, 359, 843), as well as by a variety of cytokines and growth factors, such as interleukin-1, interleukin-6, epidermal growth factor and transforming growth factor. To date, VEGF and the VEGF family members have been reported to bind to one or more of three transmembrane receptor tyrosine kinases (Mustonen et al. *J. Cell Biol.,* 1995, 129, 895), VEGF receptor-1 (also known as flt-1 (fms-like tyrosine kinase-1)), VEGFR-2 (also known as kinase insert domain containing receptor (KDR); the murine analogue of KDR is known as fetal liver kinase-1 (flk-1)), and VEGFR-3 (also known as flt-4). KDR and flt-1 have been shown to have different signal transduction properties (Waltenberger et al. *J. Biol. Chem.* 1994, 269, 26988); Park et al. *Oncogene* 1995, 10, 135). Thus, KDR undergoes strong ligand-dependant tyrosine phosphorylation in intact cells, whereas flt-1 displays a weak response. Thus, binding to KDR is believed to be a critical requirement for induction of the full spectrum of VEGF-mediated biological responses.

In vivo, VEGF plays a central role in vasculogenesis, and induces angiogenesis and permeabilization of blood vessels. Deregulated VEGF expression contributes to the development of a number of diseases that are characterized by abnormal angiogenesis and/or hyperpermeability processes. It is believed regulation of the VEGF-mediated signal transduction cascade by some agents can provide a useful mode for control of abnormal angiogenesis and/or hyperpermeability processes.

Angiogenesis is regarded as an important prerequisite for growth of tumors beyond about 1-2 mm. Oxygen and nutrients may be supplied to cells in tumor smaller than this limit through diffusion. However, it is believed every tumor is dependent on angiogenesis for continued growth after it has reached a certain size. Tumorigenic cells within hypoxic regions of tumors respond by stimulation of VEGF production, which triggers activation of quiescent endothelial cells to stimulate new blood vessel formation. (Shweiki et al. *Proc. Nat'l. Acad. Sci.,* 1995, 92, 768). In addition, VEGF production in tumor regions where there is no angiogenesis may proceed through the ras signal transduction pathway (Grugel et al. *J. Biol. Chem.,* 1995, 270, 25915; Rak et al. *Cancer Res.* 1995, 55, 4575). In situ hybridization studies have demonstrated VEGF mRNA is strongly upregulated in a wide variety of human tumors, including lung (Mattern et al. *Br. J. Cancer* 1996, 73, 931), thyroid (Viglietto et al. *Oncogene* 1995, 11, 1569), breast (Brown et al. *Human Pathol.* 1995, 26, 86), gastrointestinal tract (Brown et al. *Cancer Res.* 1993, 53, 4727; Suzuki et al. *Cancer Res.* 1996, 56, 3004), kidney and bladder (Brown et al. *Am. J. Pathol.* 1993, 1431, 1255), ovary (Olson et al. *Cancer Res.* 1994, 54, 1255), and cervical (Guidi et al. *J. Nat'l Cancer Inst.* 1995, 87, 12137) carcinomas, as well as angiosacroma (Hashimoto et al. *Lab. Invest.* 1995, 73, 859) and several intracranial tumors (Plate et al. *Nature* 1992, 359, 845; Phillips et al. *Int. J. Oncol.* 1993, 2, 913; Berkman et al. *J. Clin. Invest.,* 1993, 91, 153). Neutralizing monoclonal antibodies to KDR have been shown to be efficacious in blocking tumor angiogenesis (Kim et al. *Nature* 1993, 362, 841; Rockwell et al. *Mol. Cell. Differ.* 1995, 3, 315).

Overexpression of VEGF, for example under conditions of extreme hypoxia, can lead to intraocular angiogenesis, resulting in hyperproliferation of blood vessels, leading eventually to blindness. Such a cascade of events has been observed for a number of retinopathies, including diabetic retinopathy, ischemic retinal-vein occlusion, and retinopathy of prematurity (Aiello et al. *New Engl. J. Med.* 1994, 331, 1480; Peer et al. *Lab. Invest.* 1995, 72, 638), and age-related macular degeneration (AMD; see, Lopez et al. *Invest. Opththalmol. Vis. Sci.* 1996, 37, 855).

In rheumatoid arthritis (RA), the in-growth of vascular pannus may be mediated by production of angiogenic factors. Levels of immunoreactive VEGF are high in the synovial fluid of RA patients, while VEGF levels were low in the synovial fluid of patients with other forms of arthritis of with degenerative joint disease (Koch et al. *J. Immunol.* 1994, 152, 4149). The angiogenesis inhibitor AGM-170 has been shown to prevent neovascularization of the joint in the rat collagen arthritis model (Peacock et al. *J. Exper. Med.* 1992, 175, 1135).

Increased VEGF expression has also been shown in psoriatic skin, as well as bullous disorders associated with subepidermal blister formation, such as bullous pemphigoid, erythema multiforme, and dermatitis herpetiformis (Brown et al. *J. Invest. Dermatol.* 1995, 104, 744).

The vascular endothelial growth factors (VEGF, VEGF-C, VEGF-D) and their receptors (VEGFR2, VEGFR3) are not only key regulators of tumor angiogenesis, but also lymphangiogenesis. VEGF, VEGF-C and VEGF-D are expressed in most tumors, primarily during periods of tumor growth and, often at substantially increased levels. VEGF expression is stimulated by hypoxia, cytokines, oncogenes such as ras, or by inactivation of tumor suppressor genes (McMahon, G. *Oncologist* 2000, 5(Suppl. 1), 3-10; McDonald, N. Q.; Hendrickson, W. A. *Cell* 1993, 73, 421-424).

The biological activities of the VEGFs are mediated through binding to their receptors. VEGFR3 (also called Flt-4) is predominantly expressed on lymphatic endothelium in normal adult tissues. VEGFR3 function is needed for new lymphatic vessel formation, but not for maintenance of the pre-existing lymphatics. VEGFR3 is also upregulated on blood vessel endothelium in tumors. Recently VEGF-C and VEGF-D, ligands for VEGFR3, have been identified as regulators of lymphangiogenesis in mammals. Lymphangiogenesis induced by tumor-associated lymphangiogenic factors could promote the growth of new vessels into the tumor, providing tumor cells access to systemic circulation. Cells that invade the lymphatics could find their way into the bloodstream via the thoracic duct. Tumor expression studies have allowed a direct comparison of VEGF-C, VEGF-D and VEGFR3 expression with clinicopathological factors that relate directly to the ability of primary tumors to spread (e.g., lymph node involvement, lymphatic invasion, secondary metastases, and disease-free survival). In many instances, these studies demonstrate a statistical correlation between the expression of lymphangiogenic factors and the ability of a primary solid tumor to metastasize (Skobe, M. et al. *Nature Med.* 2001, 7(2), 192-198; Stacker, S. A. et al. *Nature Med.* 2001, 7(2), 186-191; Makinen, T. et al. *Nature Med.* 2001, 7(2), 199-205; Mandriota, S. J. et al. *EMBO J.* 2001, 20(4), 672-82; Karpanen, T. et al. *Cancer Res.* 2001, 61(5), 1786-90; Kubo, H. et al. *Blood* 2000, 96(2), 546-53).

Hypoxia appears to be an important stimulus for VEGF production in malignant cells. Activation of p38 MAP kinase is required for VEGF induction by tumor cells in response to hypoxia (Blaschke, F. et al. *Biochem. Biophys. Res. Commun.* 2002, 296, 890-896; Shemirani, B. et al. *Oral Oncology* 2002, 38, 251-257). In addition to its involvement in angiogenesis through regulation of VEGF secretion, p38 MAP kinase promotes malignant cell invasion, and migration of different tumor types through regulation of collagenase activity and urokinase plasminogen activator expression (Laferriere, J. et al. *J. Biol. Chem.* 2001, 276, 33762-33772; Westermarck, J. et al. *Cancer Res.* 2000, 60, 7156-7162; Huang, S. et al. *J. Biol. Chem.* 2000, 275, 12266-12272; Simon, C. et al. *Exp. Cell Res.* 2001, 271, 344-355).

Some diarylureas have been described as having activity as serine-threonine kinase and/or as tyrosine kinase inhibitors. The utility of these diarylureas as an active ingredient in pharmaceutical compositions for the treatment of cancer, angiogenesis disorders, and inflammatory disorders has been demonstrated. See Redman et al., *Bioorg. Med. Chem. Lett.* 2001, 11, 9-12; Smith et al., *Bioorg. Med. Chem. Lett.* 2001, 11, 2775-2778; Dumas et al., *Bioorg. Med. Chem. Lett.* 2000, 10, 2047-2050; Dumas et al., *Bioorg. Med. Chem. Lett.* 2000, 10, 2051-2054; Ranges et al., *Book of Abstracts, 220$^{th}$ ACS National Meeting, Washington, D.C., USA*, MEDI 149; Dumas et al., *Bioorg. Med. Chem. Lett.* 2002, 12, 1559-1562; Lowinger et al., *Clin. Cancer Res.* 2000, 6(suppl.), 335; Lyons et al., *Endocr.-Relat. Cancer* 2001, 8, 219-225, Riedl et al., *Book of Abstracts, 92$^{nd}$ AACR Meeting, New Orleans, La., USA*, abstract 4956; Khire et al., *Book of Abstracts, 93$^{rd}$ AACR Meeting, San Francisco, Calif., USA*, abstract 4211; Lowinger et al., *Curr. Pharm. Design* 2002, 8, 99-110; Regan et al., *J. Med. Chem.* 2002, 45, 2994-3008; Pargellis et al., *Nature Struct. Biol.* 2002, 9(4), 268-272; Carter et al., *Book of Abstracts, 92$^{nd}$ AACR Meeting, New Orleans, La., USA*, abstract 4954; Vincent et al., *Book of Abstracts, 38$^{th}$ ASCO Meeting, Orlando, Fla., USA*, abstract 1900; Hilger et al., *Book of Abstracts, 38$^{th}$ ASCO Meeting, Orlando, Fla., USA*, abstract 1916; Moore et al., *Book of Abstracts, 38$^{th}$ ASCO Meeting, Orlando, Fla., USA*, abstract 1816; Strumberg et al., *Book of Abstracts, 38$^{th}$ ASCO Meeting, Orlando, Fla., USA*, abstract 121; Madwed J B: *Book of Abstracts, Protein Kinases: Novel Target Identification and Validation for Therapeutic Development, San Diego, Calif., USA*, March 2002; Roberts et al., *Book of Abstracts, 38$^{th}$ ASCO Meeting, Orlando, Fla., USA*, abstract 473; Tolcher et al., *Book of Abstracts, 38$^{th}$ ASCO Meeting, Orlando, Fla., USA*, abstract 334; and Karp et al., *Book of Abstracts, 38$^{th}$ AACR Meeting, San Francisco, Calif., USA*, abstract 2753.

Despite the advancements in the art, there remains a need for additional treatments.

SUMMARY OF THE INVENTION

The present invention pertains to:

(i) novel compounds, salts, metabolites and prodrugs thereof, including diastereoisomeric forms, (ii) pharmaceutical compositions containing any of such compounds salts, metabolites and prodrugs thereof, including diastereoisomeric forms, and (iii) use of those compounds or compositions for treating diseases, e.g., hyper-proliferative and angiogenesis disorders, as a sole agent or in combination with other active ingredients, e.g., cytotoxic therapies.

The compounds of formula (I), salts, metabolites and prodrugs thereof, including diastereoisomeric forms (both isolated stereoisomers and mixtures of stereoisomers) are collectively referred to herein as the "compounds of the invention". Formula (I) is as follows:

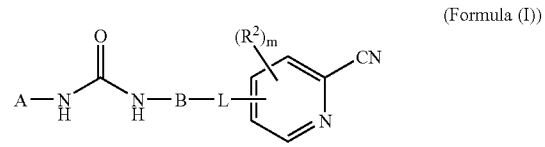

(Formula (I))

wherein

A is optionally substituted (unsubstituted and substituted)
   pyridinyl,
   naphthyl,
   8-10 membered bicyclic heteroaryl groups having 1-4 heteroatoms which are O, N, S or combinations thereof,
   partially saturated $C_8$-$C_{10}$ bicyclic carbocyclic moieties, bound to the urea moiety through a benzene group, or
   partially saturated 8 to 10 membered bicyclic heterocyclic moieties, said heterocyclic moieties having 1-4 heteroatoms which are O, N or S or combinations thereof.

Where A of Formula (I) is a partially saturated 8 to 10 membered bicyclic heterocyclic moiety with at least one oxygen atom, it is preferably substituted, more preferably halo-substituted. The halogen substituents are preferably located on the saturated carbons atoms of the partially saturated 8 to 10 membered bicyclic heterocyclic moieties. These saturated carbons atoms are more preferably per-halosubstituted, most preferably fluoro-substituted.

Structures of optionally substituted pyridinyl moieties for A of formula (I) which are of particular interest include structures of formula 1x:

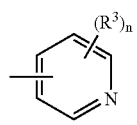

1x

Structures of optionally substituted naphthyl moieties for A of formula (I) which are of particular interest include structures of formula 1y:

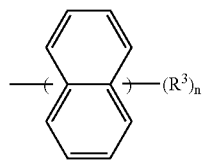

1y

The structure 1y represents that the substituents $R^3$ can appear on any carbon atom in either ring which has a valence that is otherwise complete with a hydrogen atom as a substituent. The bond to the urea group can also be through any carbon atom on either ring which has a valence that is otherwise complete with a hydrogen atom as a substituent.

Examples of suitable optionally substituted 8-10 membered bicyclic heteroaryl groups for A of formula (I) include:

2-, 3-, 4-, 5-, 6-, 7- or 8-quinolinyl,
1-, 3-, 4-, 5-, 6-, 7-, 8-isoquinolinyl,
benzimidazol-5-yl, benzimidazol-6-yl,
1,3-benzothiazol-2-yl, 1,3-benzothiazol-5-yl, 1,3-benzothiazol-6-yl,
1,2,3-benzotriazol-5-yl,
1,3-benzoxazol-2-yl, 1,3-benzoxazol-6-yl,
quinoxalin-2-yl, quinoxalin-6-yl,
1H-indazol-5-yl, 2H-indazol-5-yl, 1H-indazol-6-yl and 1H-indol-5-yl.

Structures of optionally substituted 8-10 membered bicyclic heteroaryl groups for A of formula (I) which are of particular interest include structures of formulae 1a, 1b and 1c:

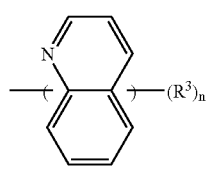

1a

-continued

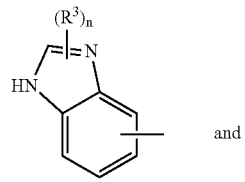

1b and

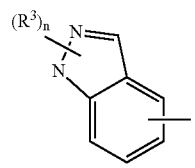

1c

The structure 1a represents that the substituents $R^3$ can appear on any carbon in either ring which has a valence that is otherwise complete with a hydrogen atom as a substituent. The bond to the urea group can also be through any carbon atom on either ring which has a valence that is otherwise complete with a hydrogen atom as a substituent.

The structures 1b and 1c represent that the substituents $R^3$ can appear on any atom in the five membered ring which has a valence that is otherwise complete with a hydrogen atom as a substituent. The bond to the urea group can be through any carbon on the six membered ring which has a valence that is otherwise complete with a hydrogen substituent.

Examples of partially saturated $C_8$-$C_{10}$ bicyclic carbocyclic moieties, bound to the urea moiety through a benzene group include 2,3-dihydro-1H-inden-4-yl and 2,3-dihydro-1H-inden-5-yl.

Structures of partially saturated $C_8$-$C_{10}$ bicyclic carbocyclic moieties for A of formula (I) which are of particular interest include structures 1d and 1e:

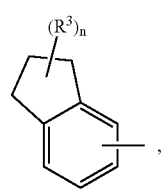

1d

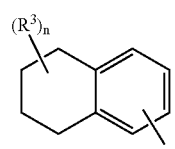

1e

The structures 1d and 1e represent that the substituents $R^3$ can appear on any carbon atom in the unsaturated ring which has a valence that is otherwise complete with a hydrogen atom as a substituent. The bond to the urea group can be through any carbon atom on the unsaturated six membered ring which has a valence that is otherwise complete with a hydrogen atom as a substituent.

Examples of partially saturated 8 to 10 membered bicyclic heterocyclic moieties having 1-4 heteroatoms which are N, S or combinations there of include 2,3-dihydro-1H-indol-5-yl and 2,3-dihydro-1H-indol-6-yl.

Examples of partially saturated 8 to 10 membered bicyclic heterocyclic moieties having 1-4 heteroatoms which are O, N, S or combinations thereof with at least one oxygen atom include:

2H,3H-benzo[e]1,4-dioxan-6-yl,
1,1-dioxido-2,3-dihydro-1-benzothien-6-yl,
1-oxo-2,3-dihydro-1H-inden-5-yl,
2H-benzo[d]1,3-dioxolen-5-yl,
2H-benzo[d]1,3-dioxolen-4-yl,
2,3-dihydrobenzo[b]fur-5-yl,
2H,4H-benzo[e]1,3-dioxan-6-yl, or
2H,4H-benzo[e]1,3-dioxan-8-yl.

These moieties can be halosubstituted, preferably at the saturated carbon atoms, up to per-halosubstitution.

Structures of partially saturated 8 to 10 membered bicyclic heterocyclic moieties for A of formula (I) which are of particular interest include structures 1f, 1g, 1h and 1i:

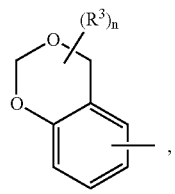

1f

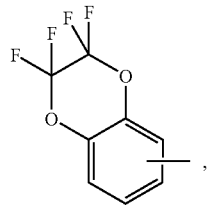

1g

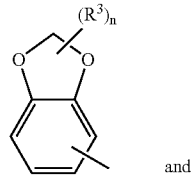

1h and

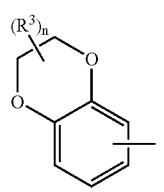

1i

The structures 1f, 1d, 1h and 1i represent that the substituents $R^3$ can appear on any carbon atom in the unsaturated ring which has a valence that is otherwise complete with a hydrogen atom as a substituent. The bond to the urea group can be through any carbon atom on the unsaturated six membered ring which has a valence that is otherwise complete with a hydrogen atom as a substituent.

B is optionally substituted phenyl or naphthyl. Structures of optionally substituted phenyl or naphthyl moieties for B of formula (I) which are of particular interest include structures 2a and 2b:

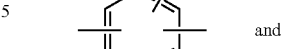

and

2a

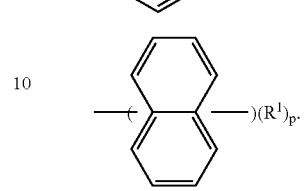

2b

The structures 2a and 2b represent that the substituents $R^1$ can appear on any carbon atom in the structure which has a valence that is otherwise complete with a hydrogen atom as a substituent and the bond to the urea group can be through any carbon atom in the structure which has a valence that is otherwise complete with a hydrogen atom as a substituent.

In a class of embodiments of this invention, B is substituted by at least one halogen substituent.

L is a bridging group which is —S— or —O—.
The variable p is 0, 1, 2, 3, or 4, typically 0 or 1.
The variable n is 0, 1, 2, 3, 4, 5 or 6, typically 0, 1, 2, 3 or 4.
The variable m is 0, 1, 2 or 3, typically 0.
Each $R^1$ is independently:
　halogen,
　$C_{1-5}$ haloalkyl,
　$NO_2$,
　$C(O)NR^4R^5$,
　$C_{1-6}$ alkyl,
　$C_{1-6}$ dialkylamine,
　$C_{1-3}$ alkylamine,
　CN,
　amino,
　hydroxy or
　$C_{1-3}$ alkoxy.

Where present, $R^1$ is more commonly halogen and of the halogens, typically chlorine or fluorine, and more commonly fluorine.

Each $R^2$ is independently:
　$C_{1-5}$ alkyl,
　$C_{1-5}$ haloalkyl,
　$C_{1-3}$ alkoxy,
　N-oxo or N-hydroxy.

Where present, $R^2$ is typically methyl or trifluoromethyl.

Each $R^3$ is independently selected from
　halogen,
　$R^4$,
　$OR^4$,
　$S(O)R^4$,
　$C(O)R^4$,
　$C(O)NR^4R^5$,
　oxo,
　cyano or
　nitro ($NO_2$).

Preferably, at least one $R^3$ is halogen. In certain embodiments, each R3 is halogen.

$R^4$ and $R^5$ are independently selected from
　hydrogen,
　$C_{1-6}$ alkyl, and
　up to per-halogenated $C_{1-6}$ alkyl.

Other examples of A include:

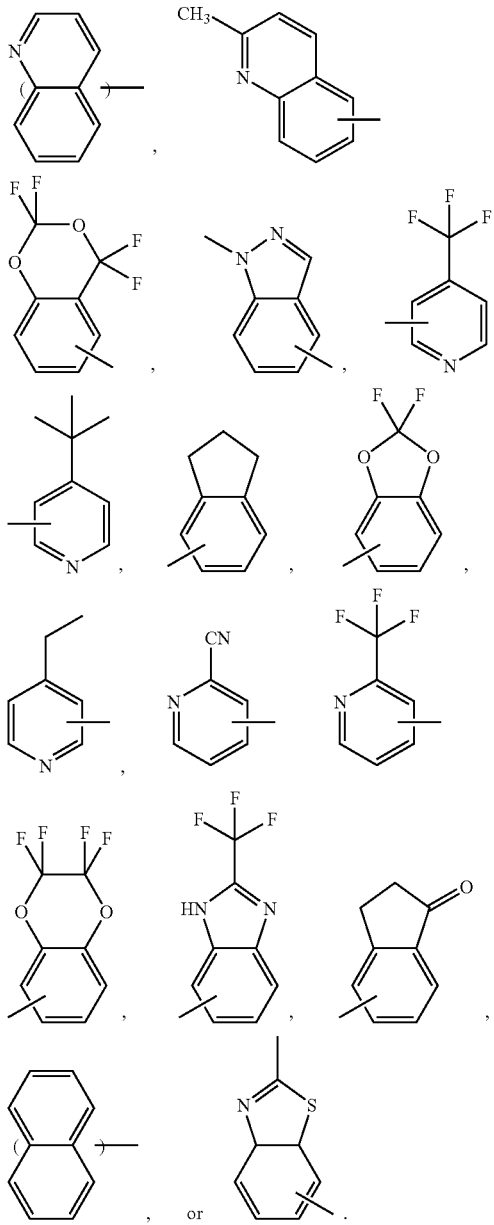

Other examples of B include

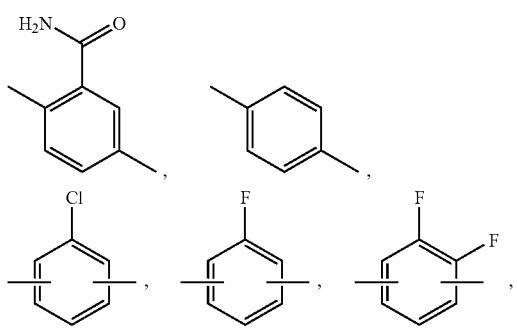

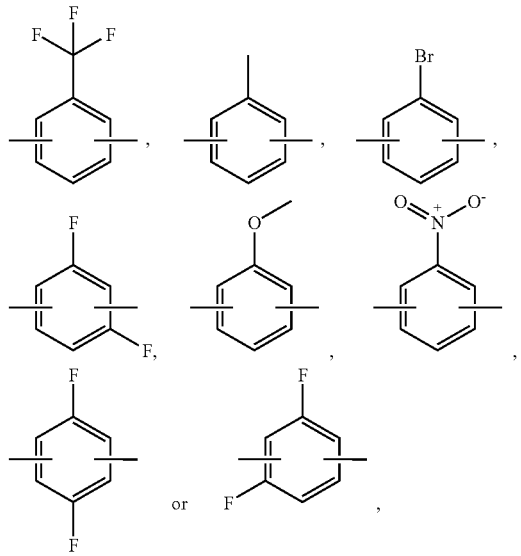

Preferably the urea group —NH—C(O)—NH— and the bridging group, L, are not bound to contiguous ring carbons of B, but rather have 1 or 2 ring carbons separating them.

Examples of $R^1$ groups include fluorine, chorine, bromine, methyl, $NO_2$, $C(O)NH_2$, methoxy, $SCH_3$, trifluoromethyl, and methanesulfonyl.

Examples of $R^2$ groups include methyl, ethyl, propyl, oxygen, and cyano.

Examples of $R^3$ groups include trifluoromethyl, methyl, ethyl, propyl, butyl, isopropyl, tert-butyl, chlorine, fluorine, bromine, cyano, methoxy, acetyl, trifluoromethanesulfonyl, trifluoromethoxy, and trifluoromethylthio.

Compounds of formula (I) of interest are:
{[2-chloro-4-(2-cyano(4-pyridyloxy))phenyl]amino}-N-indan-5-ylcarboxamide;
{[4-(2-cyano(4-pyridyloxy))-2-fluorophenyl]amino}-N-indan-5-ylcarboxamide;
{[2-chloro-4-(2-cyano(4-pyridyloxy))phenyl]amino}-N-(1-oxoindan-5-yl)carboxamide;
{[4-(2-cyano(4-pyridyloxy))-2-fluorophenyl]amino}-N-(2-naphthyl)carboxamide;
N-(2,2-difluorobenzo[d]1,3-dioxolan-5-yl){[4-(2-cyano(4-pyridyloxy))phenyl]amino}carboxamide;
N-(2,2-difluorobenzo[d]1,3-dioxolan-5-yl){[4-(2-cyano(4-pyridyloxy))phenyl]amino}carboxamide;
N-(2,2-difluorobenzo[d]1,3-dioxolan-5-yl){[2-chloro-4-(2-cyano(4-pyridyloxy))phenyl]amino}carboxamide;
N-(2,2-difluorobenzo[d]1,3-dioxolan-5-yl){[3-chloro-4-(2-cyano(4-pyridyloxy))phenyl]amino}carboxamide;
N-(2,2-difluorobenzo[d]1,3-dioxolan-5-yl){[3-chloro-4-(2-cyano(4-pyridyloxy))phenyl]amino}carboxamide;
N-(2,2-difluorobenzo[d]1,3-dioxolan-5-yl){[4-(2-cyano(4-pyridyloxy))-3-fluorophenyl]amino}carboxamide;
{[4-(2-cyano(4-pyridyloxy))-2-(trifluoromethyl)phenyl]amino}-N-(2,2,3,3-tetrafluorobenzo[e]1,4-dioxan-6-yl)carboxamide;
{[2-chloro-4-(2-cyano(4-pyridyloxy))phenyl]amino}-N-(2,2,3,3-tetrafluorobenzo[e]1,4-dioxan-6-yl)carboxamide;
{[4-(2-cyano(4-pyridyloxy))-2-fluorophenyl]amino}-N-(2,2,3,3-tetrafluorobenzo[e]1,4-dioxan-6-yl)carboxamide;

{[4-(2-cyano(4-pyridyloxy))-2,6-difluorophenyl]amino}-N-(2,2,3,3-tetrafluorobenzo[e]1,4-dioxan-6-yl)carboxamide;

{[4-(2-cyano(4-pyridyloxy))-2,5-difluorophenyl]amino}-N-(2,2,3,3-tetrafluorobenzo[e]1,4-dioxan-6-yl)carboxamide;

{[3-chloro-4-(2-cyano(4-pyridyloxy))phenyl]amino}-N-(2,2,3,3-tetrafluorobenzo[e]1,4-dioxan-6-yl)carboxamide;

{[4-(2-cyano(4-pyridyloxy))-2-methylphenyl]amino}-N-(2,2,3,3-tetrafluorobenzo[e]1,4-dioxan-6-yl)carboxamide;

{[4-(2-cyano(4-pyridyloxy))-3-methylphenyl]amino}-N-(2,2,3,3-tetrafluorobenzo[e]1,4-dioxan-6-yl)carboxamide;

{[4-(2-cyano(4-pyridyloxy))-2-nitrophenyl]amino}-N-(2,2,3,3-tetrafluorobenzo[e]1,4-dioxan-6-yl)carboxamide;

{[4-(2-cyano(4-pyridyloxy))phenyl]amino}-N-(2,2,4,4-tetrafluorobenzo[3,4-e]1,3-dioxan-6-yl)carboxamide;

{[4-(2-cyano(4-pyridyloxy))-2-fluorophenyl]amino}-N-(2,2,4,4-tetrafluorobenzo[3,4-e]1,3-dioxan-6-yl)carboxamide;

{[3-chloro-4-(2-cyano(4-pyridyloxy))phenyl]amino}-N-(2,2,4,4-tetrafluorobenzo[3,4-e]1,3-dioxan-6-yl)carboxamide;

{[2-chloro-4-(2-cyano(4-pyridyloxy))phenyl]amino}-N-(2,2,4,4-tetrafluorobenzo[3,4-e]1,3-dioxan-6-yl)carboxamide;

{[4-(2-cyano(4-pyridyloxy))-3-fluorophenyl]amino}-N-(2,2,4,4-tetrafluorobenzo[3,4-e]1,3-dioxan-6-yl)carboxamide;

{[4-(2-cyano(4-pyridyloxy))-2-(trifluoromethyl)phenyl]amino}-N-(2,2,4,4-tetrafluorobenzo[3,4-e]1,3-dioxan-6-yl)carboxamide;

{[4-(2-cyano(4-pyridyloxy))-2,3-difluorophenyl]amino}-N-(2,2,4,4-tetrafluorobenzo[3,4-e]1,3-dioxan-6-yl)carboxamide;

{[4-(2-cyano(4-pyridyloxy))-2,5-difluorophenyl]amino}-N-(2,2,4,4-tetrafluorobenzo[3,4-e]1,3-dioxan-6-yl)carboxamide;

{[4-(2-cyano(4-pyridyloxy))-2,6-difluorophenyl]amino}-N-(2,2,4,4-tetrafluorobenzo[3,4-e]1,3-dioxan-6-yl)carboxamide;

{[4-(2-cyano(4-pyridyl)oxy)-3-methoxyphenyl]amino}-N-(2,2,4,4-tetrafluorobenzo[3,4-e]1,3-dioxan-6-yl)carboxamide;

{[3-bromo-4-(2-cyano(4-pyridyloxy))phenyl]amino}-N-(2,2,4,4-tetrafluorobenzo[3,4-e]1,3-dioxan-6-yl)carboxamide;

{[4-(2-cyano(4-pyridyloxy))-2-methylphenyl]amino}-N-(2,2,4,4-tetrafluorobenzo[3,4-e]1,3-dioxan-6-yl)carboxamide;

{[4-(2-cyano(4-pyridyloxy))-3-methylphenyl]amino}-N-(2,2,4,4-tetrafluorobenzo[3,4-e]1,3-dioxan-6-yl)carboxamide;

5-(2-cyano(4-pyridyl)oxy)-2-{[N-(2,2,4,4-tetrafluorobenzo[3,4-e]1,3-dioxan-6-yl)carbamoyl]amino}benzamide {[4-(2-cyano(4-pyridyloxy))-2-nitrophenyl]amino}-N-(2,2,4,4-tetrafluorobenzo[3,4-e]1,3-dioxan-6-yl)carboxamide;

{[4-(2-cyano-1-hydroxy(4-pyridyloxy))phenyl]amino}-N-(2,2,4,4-tetrafluorobenzo[3,4-e]1,3-dioxan-6-yl)carboxamide;

{[4-(2-cyano-1-hydroxy(4-pyridyloxy))-2-fluorophenyl]amino}-N-(2,2,4,4-tetrafluorobenzo[3,4-e]1,3-dioxan-6-yl)carboxamide;

{[4-(2-cyano(4-pyridyl)oxy)-2-methylthiophenyl]amino}-N-(2,2,4,4-tetrafluorobenzo[3,4-e]1,3-dioxan-6-yl)carboxamide;

{[4-(2-cyano(4-pyridyl)oxy)-2-(methylsulfonyl)phenyl]amino}-N-(2,2,4,4-tetrafluorobenzo[3,4-e]1,3-dioxan-6-yl)carboxamide;

{[4-(2-cyano(4-pyridyloxy))-2-fluorophenyl]amino}-N-[2-(trifluoromethyl)(4-pyridyl)]carboxamide;

N-[4-(tert-butyl)(2-pyridyl)]{[4-(2-cyano(4-pyridyloxy))phenyl]amino}carboxamide;

N-[4-(tert-butyl)(2-pyridyl)]{[3-chloro-4-(2-cyano(4-pyridyloxy))phenyl]amino}carboxamide;

N-[4-(tert-butyl)(2-pyridyl)]{[4-(2-cyano(4-pyridyloxy))-3-fluorophenyl]amino}carboxamide;

N-[4-(tert-butyl)(2-pyridyl)]{[4-(2-cyano(4-pyridyloxy))-2-fluorophenyl]amino}carboxamide;

N-[4-(tert-butyl)(2-pyridyl)]{[3-bromo-4-(2-cyano(4-pyridyloxy))phenyl]amino}carboxamide;

2-({N-[4-(tert-butyl)(2-pyridyl)]carbamoyl}amino)-5-(2-cyano(4-pyridyl)oxy)benzamide N-[4-(tert-butyl)(2-pyridyl)]{[4-(2-cyano(4-pyridyloxy))-3-fluorophenyl]amino}carboxamide;

{[4-(2-cyano(4-pyridyloxy))-2-(trifluoromethyl)phenyl]amino}-N-[4-(trifluoromethyl)(2-pyridyl)]carboxamide;

{[4-(2-cyano(4-pyridyloxy))-2,6-difluorophenyl]amino}-N-[4-(trifluoromethyl)(2-pyridyl)]carboxamide;

{[4-(2-cyano(4-pyridyloxy))phenyl]amino}-N-[4-(trifluoromethyl)(2-pyridyl)]carboxamide;

{[4-(2-cyano(4-pyridyloxy))phenyl]amino}-N-(4-ethyl(2-pyridyl))carboxamide;

{[4-(2-cyano(4-pyridyloxy))phenyl]amino}-N-(2-methyl(6-quinolyl))carboxamide;

{[3-chloro-4-(2-cyano(4-pyridyloxy))phenyl]amino}-N-(2-methyl(6-quinolyl))carboxamide;

{[3-chloro-4-(2-cyano(4-pyridyloxy))phenyl]amino}-N-(6-quinolyl)carboxamide;

{[2-chloro-4-(2-cyano(4-pyridyloxy))phenyl]amino}-N-(6-quinolyl)carboxamide;

{[4-(2-cyano(4-pyridyloxy))-2-(trifluoromethyl)phenyl]amino}-N-(6-quinolyl)carboxamide;

{[4-(2-cyano(4-pyridyloxy))phenyl]amino}-N-(3-isoquinolyl)carboxamide;

{[4-(2-cyano(4-pyridyloxy))-2-fluorophenyl]amino}-N-(3-isoquinolyl)carboxamide;

{[3-chloro-4-(2-cyano(4-pyridyloxy))phenyl]amino}-N-(3-isoquinolyl)carboxamide;

{[4-(2-cyano(4-pyridyloxy))phenyl]amino}-N-(1-methyl(1H-indazol-5-yl))carboxamide;

{[4-(2-cyano(4-pyridyloxy))-2-fluorophenyl]amino}-N-(1-methyl(1H-indazol-5-yl))carboxamide;

{[2-chloro-4-(2-cyano(4-pyridyloxy))phenyl]amino}-N-(1-methyl(1H-indazol-5-yl))carboxamide;

{[4-(2-cyano(4-pyridyloxy))-2-(trifluoromethyl)phenyl]amino}-N-(1-methyl(1H-indazol-5-yl))carboxamide;

{[3-chloro-4-(2-cyano(4-pyridyloxy))phenyl]amino}-N-(1-methyl(1H-indazol-5-yl))carboxamide;

{[4-(2-cyano(4-pyridyloxy))phenyl]amino}-N-[2-(trifluoromethyl)benzimidazol-5-yl]carboxamide;

{[3-chloro-4-(2-cyano(4-pyridyloxy))phenyl]amino}-N-[2-(trifluoromethyl)benzimidazol-5-yl]carboxamide;

N-benzothiazol-5-yl{[4-(2-cyano(4-pyridyloxy))-2-nitrophenyl]amino}carboxamide;

{[4-(2-cyano(4-pyridyloxy))-3-methylphenyl]amino}-N-(2-methylbenzothiazol-5-yl)carboxamide; or salts thereof and stereoisomers thereof.

A class of compounds of interest are of formula II below
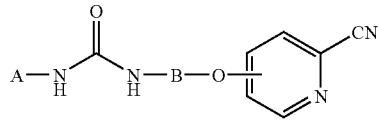
II
wherein B of formula II is
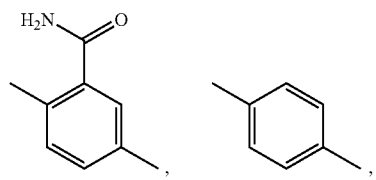,
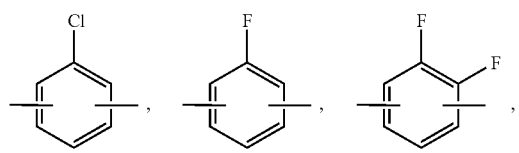,
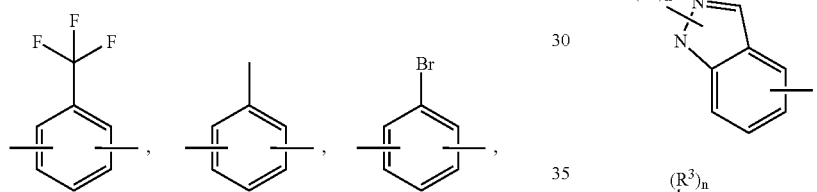,
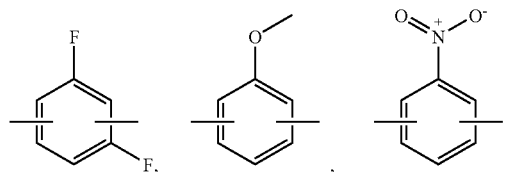,
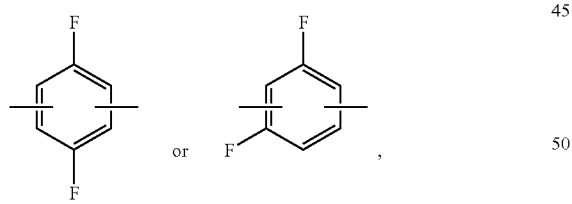 or 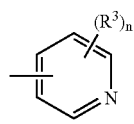,
wherein the urea group, —NH—C(O)—NH—, and the bridging group, L, are not bound to contiguous ring carbons of B, but rather have 1 or 2 ring carbons separating them,
and A of formula (II) is
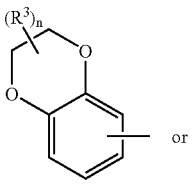 1x
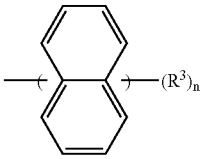 1y
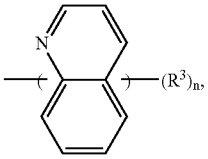 1a
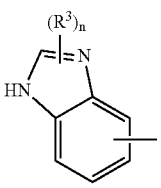 1b
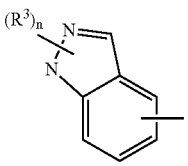 1c
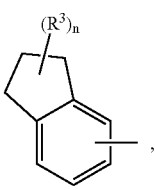 1d
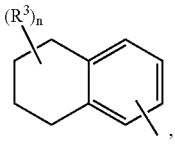 1e
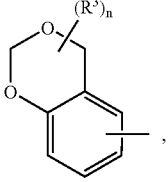 1f
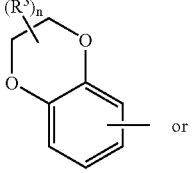 or 1i -continued

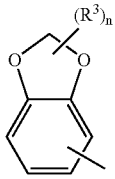
1h

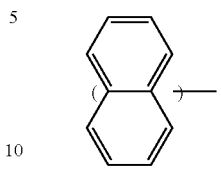 or 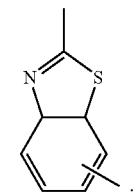

wherein the variable n is 0, 1, 2, 3 or 4, $R^3$ is trifluoromethyl, methyl, ethyl, propyl, butyl, isopropyl, tert-butyl, chlorine, fluorine, bromine, cyano, methoxy, acetyl, trifluoromethanesulfonyl, trifluoromethoxy, or trifluoromethylthio.

In a subclass of such compounds, each $R^3$ substituent on A of formula II is fluorine.

In another subclass of such compounds, A of formula II is

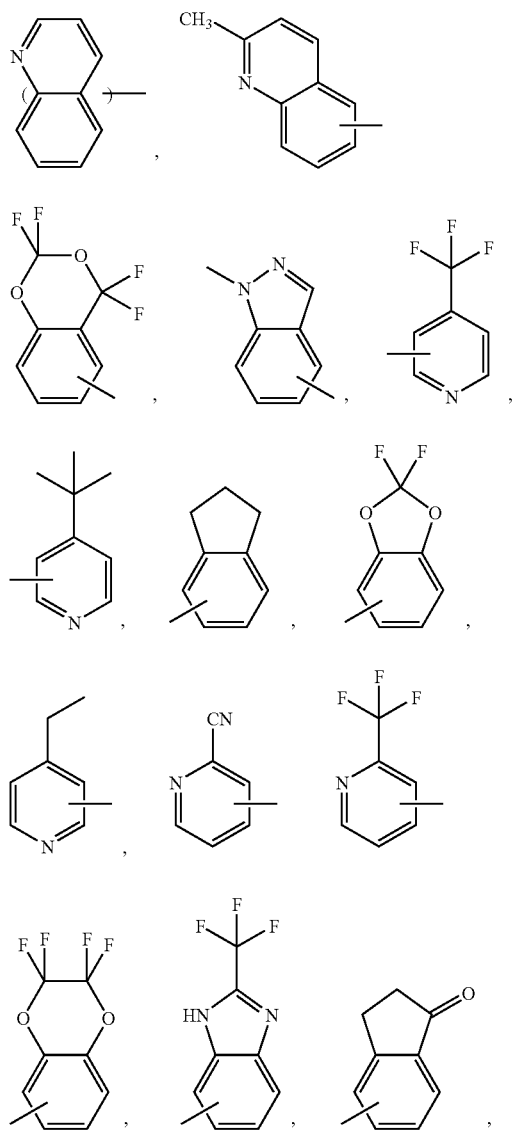

and B of formula II is phenylene, fluoro substituted phenylene or difluoro substituted phenylene.

Another class of compounds of interest includes compounds having the structures of formulae X and Y below wherein phenyl ring "B" and moiety Q each have at least one halogen substituent, preferably Cl or F, more preferably F. In a subclass of these compounds, phenyl ring "B" and moiety Q each have 2-4 halogen substituents, preferably Cl or F, more preferably F.

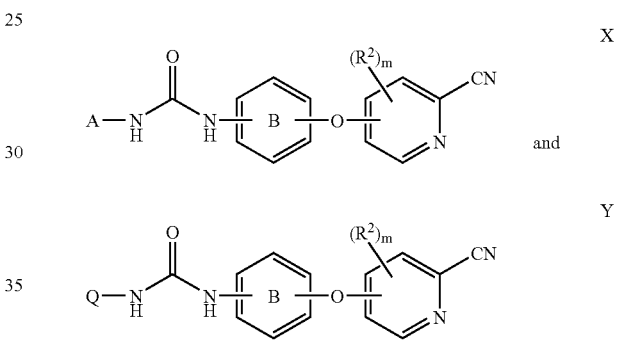

For the compounds of formula X, $R^2$, m and A are as defined above for formula I. The variable "m" is preferably zero, leaving CN as the only substituent on the pyridinyl moiety. Preferred values for A are substituted pyridinyl and partially unsaturated 8-10 member heterocyclics which have at least one oxygen heteroatom and at least one halogen substituent.

For the compounds of formula Y, $R^2$ and m are as defined above for the compounds of formula I with "m" preferably being zero.

The moiety Q represents a 8 to 10 membered bicyclic heterocyclic moiety having 1-4 heteroatoms which are O, N, S or combinations thereof. Preferably the bicyclic structure is partially unsaturated and has at least one oxygen hetero atom. In preferred embodiments, the unsaturated carbon atoms are per-halogenated.

Examples of such structures include:
2,2,4,4-tetrafluorobenzo[3,4-e]1,3-dioxan-6-yl,
2,2,3,3-tetrafluorobenzo[e]1,4-dioxan-6-yl and
2,2-difluorobenzo[d]1,3-dioxolan-5-yl.

A subclass of compounds of interest includes compounds having the structure of formulas Za, Zb, Zc and Zd below:

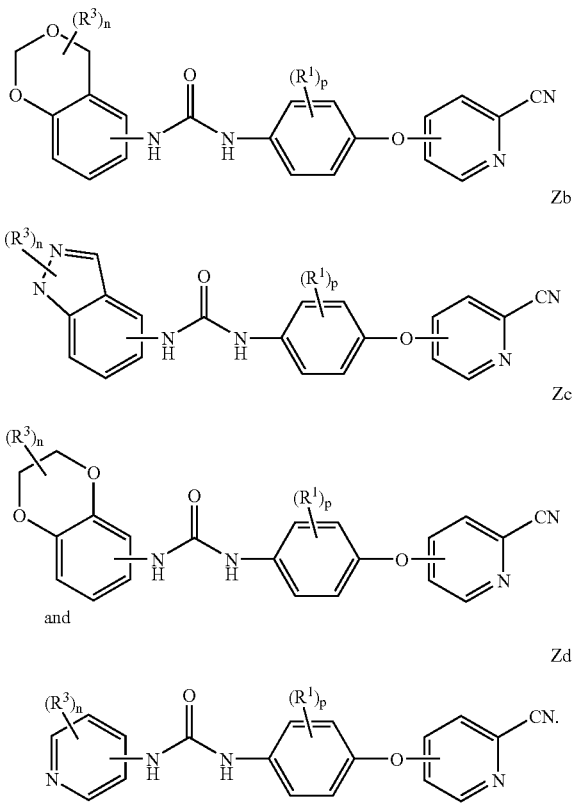

Each $R^1$ is independently halogen or trifluoromethyl and each $R^3$ is independently halogen, $R^4$, $OR^4$, $S(O)R^4$, $C(O)R^4$, $C(O)NR^4R^5$, oxo or cyano or nitro ($NO_2$) and is preferably fluoro, trifluoromethyl, methyl and t-butyl.

The variable n is 0, 1, 2, 3 or 4 and the variable p is 0 or 1.

When any moiety is "substituted", it can have up to the highest number of indicated substituents, and each substituent can be located at any available position on the moiety and can be attached through any available atom on the substituent. "Any available position" means any position on the moiety that is chemically accessible through means known in the art or taught herein and that does not create an unstable molecule, e.g., incapable of administration to a human. When there are two or more substituents on any moiety, each substituent is defined independently of any other substituent and can, accordingly, be the same or different.

The term "optionally substituted" means that the moiety so modified may be either unsubstituted, or substituted with the identified substituent(s).

It is understood that the term "hydroxy" as a pyridine substituent includes 2-, 3-, and 4-hydroxypyridine, and also includes those structures referred to in the art as 1-oxo-pyridine, 1-hydroxy-pyridine or pyridine N-oxide.

Where the plural form of the word compounds, salts, and the like, is used herein, this is taken to mean also a single compound, salt, or the like.

The term $C_{1-6}$ alkyl, unless indicated otherwise, means straight, branched chain or cyclic alkyl groups having from one to six carbon atoms, which may be cyclic, linear or branched with single or multiple branching. Such, groups include for example methyl, ethyl, n-propyl, isopropyl, n-butyl, isobutyl, sec-butyl, tert-butyl, cyclopropyl, cyclobutyl and the like.

The term $C_{1-6}$ haloalkyl, unless indicated otherwise, means a saturated hydrocarbon radical having up to six carbon atoms, which is substituted with a least one halogen atom, up to perhalo. The radical may be cyclic, linear or branched with single or multiple branching. The halo substituent(s) include fluoro, chloro, bromo, or iodo. Fluoro, chloro and bromo are preferred, and fluoro and chloro are more preferred. The halogen substituent(s) can be located on any available carbon. When more than one halogen substituent is present on this moiety, they may be the same or different. Examples of such halogenated alkyl substituents include but are not limited to chloromethyl, dichloromethyl, trichloromethyl, fluoromethyl, difluoromethyl, trifluoromethyl, 2,2,2-trifluoroethyl, and 1,1,2,2-tetrafluoroethyl, and the like.

The term $C_{1-6}$ alkoxy, unless indicated otherwise, means a cyclic, straight or branched chain alkoxy group having from one to six saturated carbon atoms which may be cyclic, linear or branched with single or multiple branching, and includes such groups as methoxy, ethoxy, n-propoxy, isopropoxy, butoxy, pentoxy and the like. It also includes halogenated groups such as 2,2-dichloroethoxy, trifluoromethoxy, and the like.

Halo or halogen means fluoro, chloro, bromo, or iodo. Fluoro, chloro and bromo are preferred, and fluoro and chloro are more preferred.

$C_{1-3}$alkylamine, unless indicated otherwise, means methylamino, ethylamino, propylamino or isopropylamino.

Examples of $C_{1-6}$ dialkylamine include but are not limited to diethylamino, ethyl-isopropylamino, methyl-isobutylamino and dihexylamino.

The term heteroaryl refers to both monocyclic and bicyclic heteroaryl rings. Monocyclic heteroaryl means an aromatic monocyclic ring having 5 to 6 ring atoms and 1-4 hetero atoms selected from N, O and S, the remaining atoms being carbon. When more than one hetero atom is present in the moiety, they are selected independently from the other(s) so that they may be the same or different. Monocyclic heteroaryl rings include, but are not limited to pyrrole, furan, thiophene, imidazole, pyrazole, thiazole, oxazole, isoxazole, isothiazole, triazole, tetrazole, thiadiazole, oxadiazole, pyridine, pyrimidine, pyridazine, pyrazine, and triazine.

Bicyclic heteroaryl means fused bicyclic moieties where one of the rings is chosen from the monocyclic heteroaryl rings described above and the second ring is either benzene or another monocyclic heteroaryl ring described above. When both rings in the bicyclic moiety are heteroaryl rings, they may be the same or different, as long as they are chemically accessible by means known in the art. Bicyclic heteroaryl rings include synthetically accessible 5-5, 5-6, or 6-6 fused bicyclic aromatic structures including, for example but not by way of limitation, benzoxazole (fused phenyl and oxazole), quinoline (fused phenyl and pyridine), imidazopyrimidine (fused imidazole and pyrimidine), and the like.

Where indicated, the bicyclic heteroaryl moieties may be partially saturated. When partially saturated either the monocyclic heteroaryl ring as described above is fully or partially saturated, the second ring as described above is either fully or partially saturated or both rings are partially saturated.

The term "5 or 6 membered heterocyclic ring, containing at least one atom selected from oxygen, nitrogen and sulfur, which is saturated, partially saturated, or aromatic" includes, by no way of limitation, tetrahydropyran, tetrahydrofuran, 1,3-dioxolane, 1,4-dioxane, morpholine, thiomorpholine, piperazine, piperidine, piperidinone, tetrahydropyrimidone, pentamethylene sulfide, tetramethylene sulfide, dihydropyrane, dihydrofuran, dihydrothiophene, pyrrole, furan, thiophene, imidazole, pyrazole, thiazole, oxazole, isoxazole, isothiazole, triazole, pyridine, pyrimidine, pyridazine, pyrazine, triazine, and the like.

The term "$C_{1-3}$ alkyl-phenyl" includes, for example, 2-methylphenyl, isopropylphenyl, 3-phenylpropyl, or 2-phenyl-1-methylethyl. Substituted examples include 2-[2-chlorophenyl]ethyl, 3,4-dimethylphenylmethyl, and the like.

Unless otherwise stated or indicated, the term "aryl" includes 6-12 membered mono or bicyclic aromatic hydrocarbon groups (e.g., phenyl, naphthalene, azulene, indene group) having 0, 1, 2, 3, 4, 5 or 6 substituents.

The compounds of Formula (I) may contain one or more asymmetric centers, depending upon the location and nature of the various substituents desired. Asymmetric carbon atoms may be present in the (R) or (S) configuration or (R,S) configuration. In certain instances, asymmetry may also be present due to restricted rotation about a given bond, for example, the central bond adjoining two substituted aromatic rings of the specified compounds. Substituents on a ring may also be present in either cis or trans form. It is intended that all such configurations (including enantiomers and diastereomers), are included within the scope of the present invention. Preferred compounds are those with the absolute configuration of the compound of Formula (I) which produces the more desirable biological activity. Separated, pure or partially purified isomers or racemic mixtures of the compounds of this invention are also included within the scope of the present invention. The purification of said isomers and the separation of said isomeric mixtures can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel O D and Chiracel O J among many others, all routinely selectable. Enzymatic separations, with or without derivitization, are also useful. The optically active compounds of Formula I can likewise be obtained by chiral syntheses utilizing optically active starting materials.

The present invention also relates to useful forms of the compounds as disclosed herein, such as pharmaceutically acceptable salts, metabolites and prodrugs of all the compounds Formula (I). The term "pharmaceutically acceptable salt" refers to a relatively non-toxic, inorganic or organic acid addition salt of a compound of the present invention. For example, see S. M. Berge, et al. "Pharmaceutical Salts," *J. Pharm. Sci.* 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts are prepared by reacting the compounds of the invention with the appropriate base via a variety of known methods.

Representative salts of the compounds of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, trifluoromethanesulfonate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aryl or aralkyl halides like benzyl and phenethyl bromides and others monosubstituted aralkyl halides or polysubstituted aralkyl halides.

Certain pharmacologically active agents can be further modified with labile functional groups that are cleaved after in vivo administration to furnish the parent active agent and the pharmacologically inactive derivatizing group. These derivatives, commonly referred to as prodrugs, can be used, for example, to alter the physicochemical properties of the active agent, to target the active agent to a specific tissue, to alter the pharmacokinetic and pharmacodynamic properties of the active agent, and to reduce undesirable side effects. Prodrugs of the invention include, e.g., the esters of appropriate compounds of this invention that are well-tolerated, pharmaceutically acceptable esters such as alkyl esters including methyl, ethyl, propyl, isopropyl, butyl, isobutyl or pentyl esters. Additional esters such as phenyl-$C_1$-$C_5$ alkyl may be used, although methyl ester is preferred.

Methods which can be used to synthesize other prodrugs are described in the following reviews on the subject, which are incorporated herein by reference for their description of these synthesis methods:

Higuchi, T.; Stella, V. eds. *Prodrugs As Novel Drug Delivery Systems*. ACS Symposium Series. American Chemical Society: Washington, D.C. (1975).

Roche, E. B. *Design of Biopharmaceutical Properties through Prodrugs and Analogs*. American Pharmaceutical Association: Washington, D.C. (1977).

Sinkula, A. A.; Yalkowsky, S. H. *J Pharm Sci.* 1975, 64, 181-210.

Stella, V. J.; Charman, W. N. Naringrekar, V. H. *Drugs* 1985, 29, 455-473.

Bundgaard, H., ed. *Design of Prodrugs*. Elsevier: New York (1985).

Stella, V. J.; Himmelstein, K. J. *J. Med. Chem.* 1980, 23, 1275-1282.
Han, H-K; Amidon, G. L. *AAPS Pharmsci* 2000, 2, 1-11.
Denny, W. A. *Eur. J. Med. Chem.* 2001, 36, 577-595.
Wermuth, C. G. in Wermuth, C. G. ed. *The Practice of Medicinal Chemistry* Academic Press: San Diego (1996), 697-715.
Balant, L. P.; Doelker, E. in Wolff, M. E. ed. *Burgers Medicinal Chemistry And Drug Discovery* John Wiley & Sons: New York (1997), 949-982.

The metabolites of the compounds of this invention include oxidized derivatives of the compounds of Formula I, II, X, Y, Za, Zb, Zc and Zd, wherein one or more of the nitrogens are substituted with a hydroxy group; which includes derivatives where the nitrogen atom of the pyridine group is in the oxide form, referred to in the art as 1-oxo-pyridine or has a hydroxy substituent, referred to in the art as 1-hydroxy-pyridine.

General Preparative Methods

The particular process to be utilized in the preparation of the compounds used in this embodiment of the invention depends upon the specific compound desired. Such factors as the selection of the specific substituents play a role in the path to be followed in the preparation of the specific compounds of this invention. Those factors are readily recognized by one of ordinary skill in the art.

The compounds of the invention may be prepared by use of known chemical reactions and procedures. Nevertheless, the following general preparative methods are presented to aid the reader in synthesizing the compounds of the present invention, with more detailed particular examples being presented below in the experimental section describing the working examples.

All variable groups of these methods are as described in the generic description if they are not specifically defined below. When a variable group or substituent with a given symbol is used more than once in a given structure, it is to be understood that each of these groups or substituents may be independently varied within the range of definitions for that symbol. It is recognized that compounds of the invention with each claimed optional functional group cannot be prepared with each of the below-listed methods. Within the scope of each method optional substituents are used which are stable to the reaction conditions, or the functional groups which may participate in the reactions are present in protected form where necessary, and the removal of such protective groups is completed at appropriate stages by methods well known to those skilled in the art.

The compounds of the invention can be made according to conventional chemical methods, and/or as disclosed below, from starting materials which are either commercially available or producible according to routine, conventional chemical methods. General methods for the preparation of the compounds are given below, and the preparation of representative compounds is specifically illustrated in examples.

General Methods

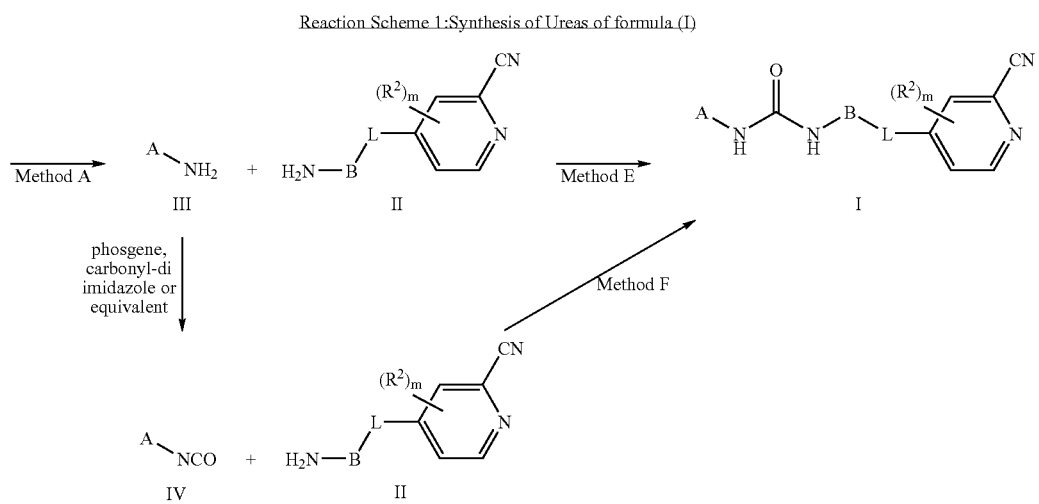

The preparation of ureas of formula (I) is depicted in Reaction Scheme 1, where A, B, L, R² are broadly defined as above. Compounds (I) can be synthesized according to the reaction sequence shown in the General Methods E and F above. Using Method E, ureas of Formula (I) are prepared from the condensation of the two arylamine fragments (II) and (III) in the presence of phosgene, di-phosgene, tri-phosgene, carbonyldiimidazole, or equivalents in a solvent that does not react with any of the starting materials. Alternatively, compounds (I) can be synthesized by reacting amino compounds (II) with isocyanate compounds (IV) using Method F.

The isocyanates (IV) are commercially available or can be synthesized from heterocyclic amines of Formula (II) or (Ill), according to methods commonly known to those skilled in the art [e.g. from treatment of an amine with phosgene or a phosgene equivalent such as trichloromethyl chloroformate (diphosgene), bis(trichloromethyl)carbonate (triphosgene), or N,N'-carbonyldiimidazole (CDI); or, alternatively by a Curtius-type rearrangement of an amide, or a carboxylic acid derivative, such as an ester, an acid halide or an anhydride].

Reaction Scheme 2: Synthesis of starting materials of formula (IV)

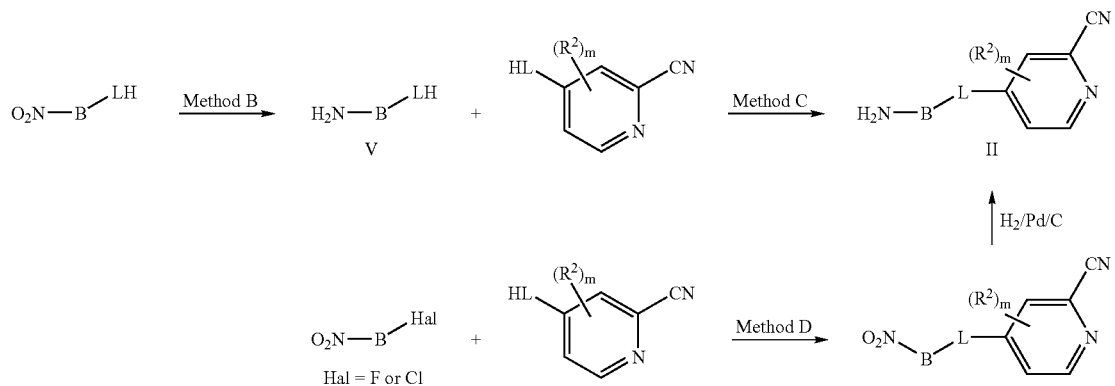

Aryl amines of formulas (III) or (V) are commercially available, or can be synthesized according to Method A or B, or methods commonly known to those skilled in the art. Aryl amines are commonly synthesized by reduction of nitroaryls using a metal catalyst, such as Ni, Pd, or Pt, and $H_2$ or a hydride transfer agent, such as formate, cyclohexadiene, or a borohydride (Rylander. *Hydrogenation Methods*; Academic Press: London, UK (1985)). Nitroaryls may also be directly reduced using a strong hydride source, such as LiAlH$_4$ (Seyden-Penne. *Reductions by the Alumino-and borohydrides in Organic Synthesis*; VCH Publishers: New York (1991)), or using a zero valent metal, such as Fe, Sn or Ca, often in acidic media. Many methods exist for the synthesis of nitroaryls (March. *Advanced Organic Chemistry*, 3$^{rd}$ Ed.; John Wiley: New York (1985). Larock. *Comprehensive Organic Transformations*; VCH Publishers: New York (1989)). Nitro aryls are commonly formed by electrophilic aromatic nitration using $HNO_3$, or an alternative $NO_2^+$ source.

For the synthesis of compounds of formula (II) where L represents —O— or —S—, and B, $R^2$ and m are broadly defined as above, the nitroaryls are further elaborated prior to reduction. In Reaction Scheme 2—method D, nitro aryls substituted with potential leaving groups such as F or Cl undergo substitution reactions on treatment with nucleophiles, such as phenoxide or thiolate, under basic conditions.

Another method for the preparation of the intermediate of Formula (II) is depicted in Reaction Scheme 2—Method C. The condensation of amine (V) with an appropriate substituted choropyridine has been previously described in the patent literatures, and can be adapted to the compounds of the present invention. For example, PCT Int. Appl., WO 99 32111, Dumas, J. et al., "Method for the Treatment of Neoplasm by inhibition of raf Kinase using N-Heteroaryl-N'-(hetero)arylureas", PCT Int. Appl., WO 99 32110, Dumas, J., et al., "Inhibition of raf Kinase using Aryl- and Heteroaryl-Substituted Heterocyclic Ureas".

Reaction Scheme 3: Alternate Synthesis of Ureas of formula (I)

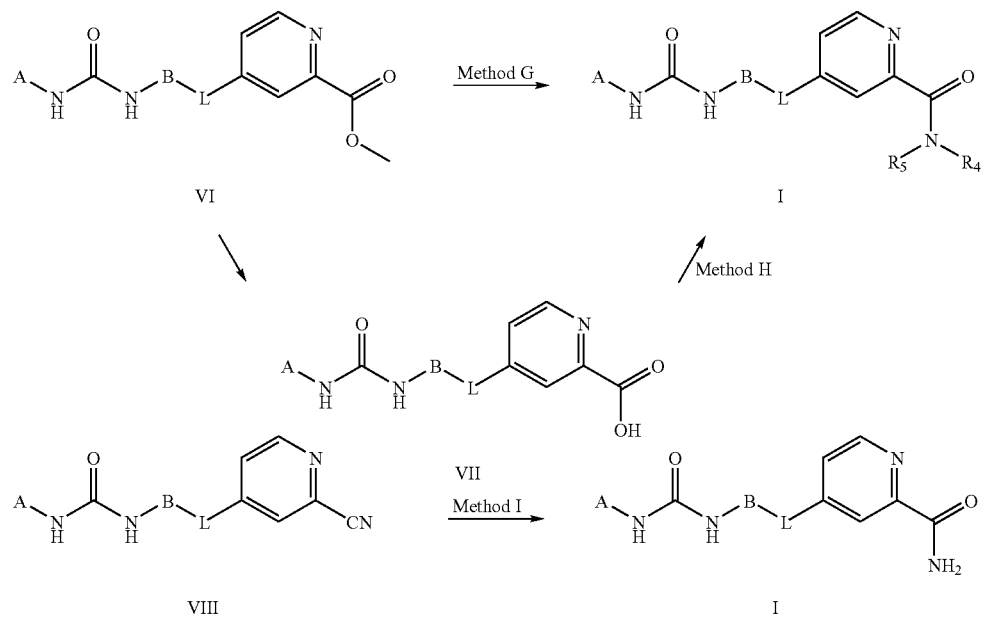

The compounds of the invention may also be prepared from compounds of formula (VII) according to the reaction sequence shown in the General Methods G and H above. Using Method G, ureas of Formula (VI) are treated with a lewis acid such as magnesium chloride and the appropriate substituted amines, in a solvent such as THF at room temperature, to provide substituted amides. In Method H, ureas of Formula (VI) are deesterified with a base such as potassium hydroxide, lithium hydroxide, or sodium hydroxide. Carboxylic acids of formula (VII) are coupled with the appropriate amines according to methods commonly known to those skilled in the art [e.g. from treatment of a carboxylic acid with DCC/DMAP or EDCI/HOBT], in a solvent such as THF, AcCN, or DMF. In addition, compounds of formula (I) where $R_4$ and $R_5$ are hydrogens may be synthesized according to the reaction scheme shown in Method I. The cyano compound (VIII) can be hydrolyzed in the presence of NaOH or sodium percarbonate, in aqueous solvent such as acetone-water, and at temperature from 20 to 100° C. Compounds of formula (VI) and (VIII) are synthesized according to methods A to F, or methods commonly known to those skilled in the art.

Pyridine-1-oxides or Formula (I) where the pyridine ring carries a hydroxy substituent on its nitrogen atom, and A, B, L are broadly defined as above can be prepared from the corresponding pyridines using oxidation conditions know in the art. Some examples are as follows:

- peracids such as meta chloroperbenzoic acids in chlorinated solvents such as dichloromethane, dichloroethane, or chloroform (Markgraf et al., *Tetrahedron* 1991, 47, 183);
- $(Me_3SiO)_2$ in the presence of a catalytic amount of perrhenic acid in chlorinated solvents such as dichloromethane (Coperet et al., *Terahedron Lett.* 1998, 39, 761);
- Perfluoro-cis-2-butyl-3-propyloxaziridine in several combinations of halogenated solvents (Amone et al., *Tetrahedron* 1998, 54, 7831);
- Hypofluoric acid—acetonitrile complex in chloroform (Dayan et al., *Synthesis* 1999, 1427);
- Oxone, in the presence of a base such as KOH, in water (Robker et al., *J. Chem. Res., Synop.* 1993, 10, 412);
- Magnesium monoperoxyphthalate, in the presence of glacial acetic acid (Klemm et al., *J. Heterocylic Chem.* 1990, 6, 1537);
- Hydrogen peroxide, in the presence of water and acetic acid (Lin A. J., *Org. Prep. Proced. Int.* 1991, 23(1), 114);
- Dimethyldioxirane in acetone (Boyd et al., *J. Chem. Soc., Perkin Trans.* 1991, 9, 2189).

In addition, specific methods for preparing diaryl ureas and intermediate compounds (II) are already described in the patent literature, and can be adapted to the compounds of the present invention. For example, Miller S. et al, "Inhibition of p38 Kinase using Symmetrical and Unsymmetrical Diphenyl Ureas" PCT Int. Appl. WO 99 32463, Miller, S et al. "Inhibition of raf Kinase using Symmetrical and Unsymmetrical Substituted Diphenyl Ureas" PCT Int. Appl., WO 99 32436, Dumas, J. et al., "Inhibition of p38 Kinase Activity using Substituted Heterocyclic Ureas" PCT Int. Appl., WO 99 32111, Dumas, J. et al., "Method for the Treatment of Neoplasm by Inhibition of raf Kinase using N-Heteroaryl-N'-(hetero)arylureas" PCT Int. Appl., WO 99 32106, Dumas, J. et al., "Inhibition of p38 Kinase Activity using Aryl- and Heteroaryl-Substituted Heterocyclic Ureas" PCT Int. Appl., WO 99 32110, Dumas, J., et al., "Inhibition of raf Kinase using Aryl and Heteroaryl-Substituted Heterocyclic Ureas" PCT Int. Appl., WO 99 32455, Riedl, B., et al., "O-Carboxy Aryl Substituted Diphenyl Ureas as raf Kinase Inhibitors" PCT Int. Appl., WO 00 42012, Riedl, B., et al., "O-Carboxy Aryl Substituted Diphenyl Ureas as p38 Kinase Inhibitors" PCT Int. Appl., WO 00 41698, Dumas, J. et al. "Heteroaryl ureas containing nitrogen hetero-atoms as p38 kinase inhibitors" U.S. Pat. Appl. Publ., US 20020065296, Dumas, J. et al. "Preparation of N-aryl-N'-[(acylphenoxy) phenyl]ureas as raf kinase inhibitors" PCT Int. Appl., WO 02 62763, Dumas, J. et al. "Inhibition of raf kinase using quinolyl, isoquinolyl or pyridyl ureas" PCT Int. Appl., WO 02 85857, Dumas, J. et al. "Preparation of quinolyl, isoquinolyl or pyridyl-ureas as inhibitors of raf kinase for the treatment of tumors and/or cancerous cell growth" U.S. Pat. Appl. Publ., US 20020165394. All the preceding patent applications are hereby incorporated by reference.

The reaction of the compounds (III) or (IV) with (II) is carried out preferably in a solvent. Suitable solvents comprise the customary organic solvents which are inert under the reaction conditions. Non-limiting examples include ethers such as diethyl ether, dioxane, tetrahydrofuran, 1,2-dimethoxy ethane; hydrocarbons such as benzene, toluene, xylene, hexane, cyclohexane, mineral oil fractions; halogenated hydrocarbons such as dichloromethane, trichloromethane, carbon tetrachloride, dichloroethane, trichloroethylene, chlorobenzene; alcohols such as methanol, ethanol, n-propanol, isopropanol; esters such as ethyl acetate; ketones such as acetone; nitriles such as acetonitrile; heteroaromatics such as pyridine; polar solvents such as dimethyl formamide and hexamethyl phosphoric acid tris-amide; and mixtures of the above-mentioned solvents. Toluene, benzene, and dichloromethane are preferred.

The compounds (III) are generally employed in an amount of from about 1 to 3 mol per mol of compounds (II); an equimolar amount or slight excess of compounds (III) is preferred.

The reaction of the compounds (II) with (III) is generally carried out within a relatively wide temperature range. In general, they are carried out in a range of from about −20 to 200° C., preferably from about 0 to 100° C., and more preferably from about 25 to 50° C. The steps of this reaction are generally carried out under atmospheric pressure. However, it is also possible to carry them out under superatmospheric pressure or under reduced pressure (for example, in a range of from about 0.5 to 5 bar). The reaction time can generally be varied within a relatively wide range. In general, the reaction is finished after a period of from about 2 to 24 hours, preferably from about 6 to 12 hours.

Synthetic transformations that may be employed in the synthesis of compounds of Formula (I) and in the synthesis of intermediates involved in the synthesis of compounds of Formula (I) are known by or accessible to one skilled in the art. Collections of synthetic transformations may be found in compilations, such as:

- J. March. *Advanced Organic Chemistry*, $4^{th}$ ed.; John Wiley: New York (1992);
- R. C. Larock. *Comprehensive Organic Transformations*, $2^{nd}$ ed.; Wiley-VCH: New York (1999);
- F. A. Carey; R. J. Sundberg. *Advanced Organic Chemistry*, $2^{nd}$ ed.; Plenum Press: New York (1984);
- T. W. Greene; P. G. M. Wuts. *Protective Groups in Organic Synthesis*, $3^{rd}$ ed.; John Wiley: New York (1999);
- L. S. Hegedus. *Transition Metals in the Synthesis of Complex Organic Molecules*, $2^{nd}$ ed.; University Science Books: Mill Valley, Calif. (1994);
- L. A. Paquette, Ed. *The Encyclopedia of Reagents for Organic Synthesis*; John Wiley: New York (1994);
- A. R. Katritzky; O. Meth-Cohn; C. W. Rees, Eds. *Comprehensive Organic Functional Group Transformations*; Pergamon Press: Oxford, UK (1995);

G. Wilkinson; F. G A. Stone; E.W. Abel, Eds. *Comprehensive Organometallic Chemistry*; Pergamon Press: Oxford, UK (1982);

B. M. Trost; I. Fleming. *Comprehensive Organic Synthesis*; Pergamon Press: Oxford, UK (1991);

A. R. Katritzky; C. W. Rees Eds. *Comprehensive Heterocylic Chemistry*; Pergamon Press: Oxford, UK (1984);

A. R. Katritzky; C. W. Rees; E. F. V. Scriven, Eds. *Comprehensive Heterocylic Chemistry II*; Pergamon Press: Oxford, UK (1996); and C. Hansch; P. G. Sammes; J. B. Taylor, Eds. *Comprehensive Medicinal Chemistry*: Pergamon Press: Oxford, UK (1990).

In addition, recurring reviews of synthetic methodology and related topics include *Organic Reactions*; John Wiley: New York; *Organic Syntheses*; John Wiley: New York; *Reagents for Organic Synthesis*: John Wiley: New York; *The Total Synthesis of Natural Products*; John Wiley: New York; *The Organic Chemistry of Drug Synthesis*; John Wiley: New York; *Annual Reports in Organic Synthesis*; Academic Press: San Diego Calif.; and *Methoden der Organischen Chemie* (Houben-Weyl); Thieme: Stuttgart, Germany. Furthermore, databases of synthetic transformations include *Chemical Abstracts*, which may be searched using either CAS OnLine or SciFinder, *Handbuch der Organischen Chemie* (Beilstein), which may be searched using SpotFire, and REACCS.

Compositions of the Compounds of this Invention

This invention also relates to pharmaceutical compositions containing one or more compounds of the present invention. These compositions can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions which are comprised of a pharmaceutically acceptable carrier and a pharmaceutically effective amount of a compound of the present invention, (the compounds of formula I, their salts, prodrugs and metabolites, including diastereoisomeric forms). A pharmaceutically acceptable carrier is preferably a carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound, preferably in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations which are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)-Part-1" *PDA Journal of Pharmaceutical Science & Technology* 1999, 53(6), 324-349; and Nema, S. et al, "Excipients and Their Use in Injectable Products" *PDA Journal of Pharmaceutical Science & Technology* 1997, 51(4), 166-171.

Commonly used pharmaceutical ingredients which can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC$—$CClF_2$ and $CClF_3$);

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate);

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection);

chelating agents (examples include but are not limited to edetate disodium and edetic acid);

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin; sorbitan monooleate, polyoxyethylene 50 monostearate);

encapsulating agents (examples include but are not limited to gelatin and cellulose acetate phthalate);

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono-or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas);

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnauba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/ml solution of the desired compound of this invention can be made using sterile, injectable water, and the pH is adjusted if necessary. The solution is diluted for administration to 1-2 mg/ml with sterile 5% dextrose and is administered as an IV infusion over 60 minutes.

Lyophilized Powder for IV Administration: A sterile preparation can be prepared with (I) 100-1000 mg of the desired compound of this invention as a lypholized powder, (ii) 32-327 mg/ml sodium citrate, and (iii) 300-3000 mg Dextran 40. The formulation is reconstituted with sterile, injectable saline or dextrose 5% to a concentration of 10 to 20 mg/ml, which is further diluted with saline or dextrose 5% to 0.2-0.4 mg/ml, and is administered either IV bolus or by IV infusion over 15-60 minutes.

Intramuscular Suspension: The following solution or suspension can be prepared, for intramuscular injection:

50 mg/ml of the desired, water-insoluble compound of this invention 5 mg/ml sodium carboxymethylcellulose 4 mg/ml TWEEN 80

9 mg/ml sodium chloride 9 mg/ml benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. Of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Hyper-Proliferative Disorders

The present invention relates to a method for using the compounds of Formula (I) as described above, including salts and esters thereof and compositions thereof, to treat mammalian hyper-proliferative disorders. This method comprises administering to a mammal in need thereof, including a human, an amount of a compound of this invention, or a pharmaceutically acceptable salt or ester thereof, which is effective to treat the disorder. Hyper-proliferative disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

Based upon standard laboratory techniques known to evaluate compounds useful for the treatment of hyper-proliferative disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg, and preferably from about 0.01 mg/kg to about 20 mg/kg body weight per day. A unit dosage may contain from about 0.5 mg to about 1500 mg of active ingredient, and can be administered for example, one or more times per day. In some cases every other day or weekly administration is suitable. Clinically useful dosing schedules will range from three times a day dosing to once every four weeks dosing. In addition, "drug holidays" in which a patient is not dosed with a drug for a certain period of time, may be beneficial to the overall balance between pharmacological effect and tolerability. The average daily dosage for administration by injection, including intravenous, intramuscular, subcutaneous and parenteral injections, and use of infusion techniques will preferably be from about 0.01 to 200 mg/kg of total body weight. The average daily rectal dosage regimen will preferably be from about 0.01 to 200 mg/kg of total body weight. The average daily vaginal dosage regimen will preferably be from about 0.01 to 200 mg/kg of total body weight. The average daily topical dosage regimen will preferably be from about 0.1 to 200 mg administered between one to four times daily. The transdermal concentration will preferably be that required to maintain an average daily dose of from about 0.01 to 200 mg/kg. The average daily inhalation dosage regimen will preferably be from about 0.01 to 100 mg/kg of total body weight.

The specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

The compounds of this invention can be administered as the sole pharmaceutical agent or in combination with one or more other pharmaceutical agents where the combination causes no unacceptable adverse effects. For example, the compounds of this invention can be combined with known anti-hyper-proliferative or other indication agents, and the like, as well as with admixtures and combinations thereof. Examples of known anti-hyper-proliferative or other indication agents, and the like, include, but are not limited to aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depomedrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lentinan sulphate, letrozole, leucovorin, leuprolide, leuprolide acetate, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, rebif, rhenium-186 etidronate, rituximab, roferon-A, romurtide, salagen, sandostatin, sargramostim, semustine, sizofiran, sobuzoxane, solumedrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, and zofran.

In addition, compounds of this invention can be administered in combination with one or more other pharmaceutical agents currently being studied for use as anti-hyper-proliferative or other indication agents, and the like, as well as with admixtures and combinations thereof. Examples of pharmaceutical agents currently being studied for use as anti-hyperproliferative or other indication agents, and the like, include, but are not limited to ABI-007, acolbifene, actimmune, affinitak, aminopterin, arzoxifene, asoprisnil, atamestane, atrasentan, BAY 43-9006, avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, and zoledronic acid.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

It is believed that one skilled in the art, using the preceding information and information available in the art, can utilize the present invention to its fullest extent.

It should be apparent to one of ordinary skill in the art that changes and modifications can be made to this invention without departing from the spirit or scope of the invention as it is set forth herein.

The topic headings set forth above and below are meant as guidance where certain information can be found in the application, but are not intended to be the only source in the application where information on such topic can be found.

All publications and patents cited above and below are incorporated herein by reference.

The present invention provides, but is not limited, to the embodiments defined in the following paragraphs:

EXAMPLES

Unless otherwise stated the reaction conditions, methods, abbreviations and reagents are listed below. All temperatures are in degrees Celsius (° C.) and all parts and percentages are by weight. Commercial grade reagents and solvents were used without further purification.

| Abbreviations used in this specification | |
|---|---|
| DBU | 1,8-diazabicyclo[5.4.0]undec-7-ene |
| DMF | N,N-dimethyl formamide |
| DCM | dichloromethane |
| DCE | 1,2-dichloroethane |
| DMSO | dimethyl sulphoxide |
| HPLC | High pressure liquid chromatography |
| MPLC | Medium pressure liquid chromatography |
| LC-MS | liquid chromatography —coupled mass spectroscopy |
| RT | retention time |
| MP | melting point |
| NMR | nuclear resonance spectroscopy |
| TLC | thin layer chromatography |
| ES | electrospray |
| DMAC | N,N-dimethylacetamide |
| HRMS | high resolution mass spectroscopy |
| CDI | 1,1'-carbonyldiimidazole |
| HOBT | 1-hydroxybenzotriazole |
| DCC | 1,3-dicyclohexylcarbodiimide |
| EDCI | 1-[3-(dimethylamino) propyl]-3-ethylcarbodiimide hydrochloride |
| DMAP | 4-dimethylaminopyridine |
| TMSCI | Trimethylsilyl chloride |
| m-CPBA | 3-chloroperbenzoic acid |
| HEPES | N-(2-hydroxyethyl)-piperazine-N'-(2-ethane sulphonic acid) |
| Tris/hydrochloric acid | tris(hydroxymethyl)-aminomethane hydrochloride |

| Abbreviations used in this specification | |
|---|---|
| ™ Triton X-100 ® | tert.-octyl-phenoxypolyethoxyethanol, Rohm & Haas, USA |

The yield percentages of the following examples refer to the starting component which was used in the lowest molar amount.

| LC-MS Methods |
|---|
| LC-MS (Method 1): |

| | | | | |
|---|---|---|---|---|
| MS equipment: | Micromass Quattro LCZ | | | |
| | ionization mode: ESI positive/negative | | | |
| HPLC equipment: | HP 1100 | | | |
| | UV detection: 208-400 nm | | | |
| | temperature: 40° C. | | | |
| Column: | ™ Symmetry C 18 | | | |
| | 50 mm × 2.1 mm 3.5 μm | | | |
| Supplier: | Waters | | | |
| Gradient: | Time | | | Flow |
| | [min.] | A: % | B: % | [mL/min.] |
| | 0.00 | 90.0 | 10.0 | 0.50 |
| | 4.00 | 10.0 | 90.0 | 0.50 |
| | 6.00 | 10.0 | 90.0 | 0.50 |

A: 0.05% strength solution of formic acid in water
B: 0.05% strength formic acid in acetonitrile

| LC-MS (Method 2): |
|---|

| | | | | |
|---|---|---|---|---|
| MS equipment: | Micromass LCZ | | | |
| | ionization mode: ESI | | | |
| HPLC equipment: | Gilson 215 | | | |
| | UV detection: 254 nm | | | |
| Column: | YMC pro C-18 | | | |
| | 23 mm × 2 mm 120 Å | | | |
| Supplier: | YMC | | | |
| Gradient: | Time | | | Flow |
| | [min.] | A: % | B: % | [mL/min.] |
| | 0.50 | 90.0 | 10.0 | 1.0 |
| | 3.50 | 5.0 | 95.0 | 1.0 |
| | 4.00 | 5.0 | 95.0 | 1.0 |
| | 4.01 | 90.0 | 10.0 | 1.0 |
| | 4.80 | 90.0 | 10.0 | 1.0 |

A: 0.02% strength solution of trifluoroacetic acid in 2% acetonitrile/98% water
B: 0.02% strength solution of trifluoroacetic acid in 98% acetonitrile/2% water

| HPLC (Method 3): |
|---|

| | | | | |
|---|---|---|---|---|
| HPLC Equipment: | Gilson 215 | | | |
| | UV Detection: 220 and 254 nM | | | |
| | Temperature: 25° C. | | | |
| Column: | YMC-Pack Pro C18 | | | |
| | 50 mm × 4.6 mm 5 □m | | | |
| Supplier: | Waters | | | |
| Gradient: | Time | | | Flow |
| | [min.] | A: % | B: % | [mL/min] |
| | 0.00 | 10.0 | 90.0 | 4.00 |
| | 3.50 | 90.0 | 10.0 | 4.00 |
| | 4.50 | 90.0 | 10.0 | 4.00 |
| | 4.60 | 10.0 | 90.0 | 4.00 |
| | 5.00 | 10.0 | 90.0 | 4.00 |

A: 0.1% strength solution of TFA in acetonitrile
B: 0.1% strength aqueous TFA

-continued

| LC-MS Methods | | | | |
|---|---|---|---|---|
| HPLC (Method 4): | | | | |
| HPLC Equipment: | Gilson 215 | | | |
| | UV Detection: 220 and 254 nM | | | |
| | Temperature: 25° C. | | | |
| Column: | YMC-Pack Pro C18 | | | |
| | 75 mm × 30 mm 5 μm | | | |
| Supplier: | Waters | | | |
| Gradient: | Time | | | Flow |
| | [min.] | A: % | B: % | [mL/min] |
| | 0.00 | 20.0 | 80.0 | 25.00 |
| | 20.00 | 80.0 | 20.0 | 25.00 |

A: acetonitrile
B: 0.1% strength aqueous TFA

Preparation of Starting Materials and Intermediates

General Method A: Preparations of Aminophenols

Aminophenols are either commercially available or may be prepared as described in one or more of the Examples below.

Method A-1

Preparation of 5-Nitroindazole-1-carboxylic acid tert-butyl ester

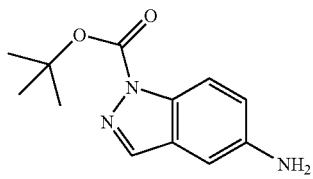

Step 1: Preparation of 5-Nitroindazole-1-carboxylic acid tert-butyl ester

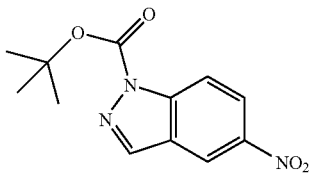

To a 0° C. slurry of 5-nitroindazole (5 g, 30.6 mmol), $Et_3N$ (4.7 mL, 33.7 mmol) and 4-dimethylaminopyridine (0.75 g, 6.1 mmol) in acetonitrile (60 mL) was added dropwise to a solution of di-tert-butyl dicarbonate (8 g, 36.8 mmol) in acetonitrile (40 mL). The resulting mixture was stirred for 30 min, then concentrated under reduced pressure. The residue was dissolved in $Et_2O$ (200 mL) and $H_2O$ (100 mL). The pH of the aqueous layer was adjusted to 2 using a 1N HCl solution. The organic phase was separated, dried ($Na_2SO_4$) and concentrated under reduced pressure to give 5-nitroindazole-1-carboxylic acid tert-butyl ester (7.8 g, 96%) as a yellow solid: TLC (30% EtOAc/hex), $R_f$=0.70; ES-LCMS (rel abundance) m/z 264 ($MH^+$, 100%).

Step 2: Preparation of the Title Compounds
5-Aminoindazole-1-carboxylic acid tert-butyl ester Palladium on carbon (780 mg) was placed under an inert atmosphere and suspended in EtOH (15 mL). A solution of 5-nitroindazole-1-carboxylic acid tert-butyl ester (7.78 g, 29.5) in EtOH (100 mL) and EtOAc (100 mL) was added. The reaction mixture was placed under $H_2$ atmosphere (1 Atm pressure) and stirred overnight. The resulting mixture was filtered through a pad of Celite®. The filtrate was concentrated under reduced pressure to yield a greenish foamy solid. The crude product was dissolved in $CH_2Cl_2$ and purified by Biotage Flash 40M (gradient from 30% to 50% EtOAc/hex) to give the title compound (6.55 g, 95%) as a white solid: TLC (50%EtOAc/hex), $R_f$=0.41; ES-LCMS (rel abundance) m/z 234 ($MH^+$, 66%).

Additional compounds illustrated in Table 1 were prepared as described above by choosing the appropriate starting materials that are readily available and/or the synthesis of which is taught herein, and using the processes of Method E described above or other standard chemical processes known in the art.

TABLE 1

Examples of preferred compounds of formula (I)

| 104 | 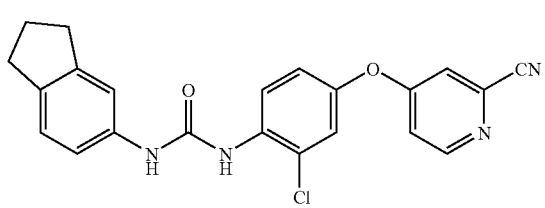 | {[2-chloro-4-(2-cyano(4-pyridyloxy))phenyl]amino}-N-indan-5-ylcarboxamide |
|---|---|---|

TABLE 1-continued

Examples of preferred compounds of formula (I)

| | | |
|---|---|---|
| 105 | | {[4-(2-cyano(4-pyridyloxy))-2-fluorophenyl]amino}-N-indan-5-ylcarboxamide |
| 106 | | {[2-chloro-4-(2-cyano(4-pyridyloxy))phenyl]amino}-N-(1-oxoindan-5-yl)carboxamide |
| 107 | | {[4-(2-cyano(4-pyridyloxy))-2-fluorophenyl]amino}-N-(2-naphthyl)carboxamide |
| 108 | | N-(2,2-difluorobenzo[d]1,3-dioxolan-5-yl){[4-(2-cyano(4-pyridyloxy))phenyl]amino}carboxamide |
| 109 | | N-(2,2-difluorobenzo[d]1,3-dioxolan-5-yl){[4-(2-cyano(4-pyridyloxy))phenyl]amino}carboxamide |
| 110 | | N-(2,2-difluorobenzo[d]1,3-dioxolan-5-yl){[2-chloro-4-(2-cyano(4-pyridyloxy))phenyl]amino}carboxamide |
| 111 | | N-(2,2-difluorobenzo[d]1,3-dioxolan-5-yl){[3-chloro-4-(2-cyano(4-pyridyloxy))phenyl]amino}carboxamide |

TABLE 1-continued

Examples of preferred compounds of formula (I)

| | | |
|---|---|---|
| 112 | | N-(2,2-difluorobenzo[d]1,3-dioxolan-5-yl){[3-chloro-4-(2-cyano(4-pyridyloxy))phenyl]amino}carboxamide |
| 113 | | N-(2,2-difluorobenzo[d]1,3-dioxolan-5-yl){[4-(2-cyano(4-pyridyloxy))-3-fluorophenyl]amino}carboxamide |
| 114 | | {[4-(2-cyano(4-pyridyloxy))-2-(trifluoromethyl)phenyl]amino}-N-(2,2,3,3-tetrafluorobenzo[e]1,4-dioxan-6-yl)carboxamide |
| 115 | | {[2-chloro-4-(2-cyano(4-pyridyloxy))phenyl]amino}-N-(2,2,3,3-tetrafluorobenzo[e]1,4-dioxan-6-yl)carboxamide |
| 116 | | {[4-(2-cyano(4-pyridyloxy))-2-fluorophenyl]amino}-N-(2,2,3,3-tetrafluorobenzo[e]1,4-dioxan-6-yl)carboxamide |

TABLE 1-continued

Examples of preferred compounds of formula (I)

| # | Structure | Name |
|---|---|---|
| 117 | | {[4-(2-cyano(4-pyridyloxy))-2,6-difluorophenyl]amino}-N-(2,2,3,3-tetrafluorobenzo[e]1,4-dioxan-6-yl)carboxamide |
| 118 | | {[4-(2-cyano(4-pyridyloxy))-2,5-difluorophenyl]amino}-N-(2,2,3,3-tetrafluorobenzo[e]1,4-dioxan-6-yl)carboxamide |
| 119 | | {[3-chloro-4-(2-cyano(4-pyridyloxy))phenyl]amino}-N-(2,2,3,3-tetrafluorobenzo[e]1,4-dioxan-6-yl)carboxamide |
| 120 | | {[4-(2-cyano(4-pyridyloxy))-2-methylphenyl]amino}-N-(2,2,3,3-tetrafluorobenzo[e]1,4-dioxan-6-yl)carboxamide |
| 121 | | {[4-(2-cyano(4-pyridyloxy))-3-methylphenyl]amino}-N-(2,2,3,3-tetrafluorobenzo[e]1,4-dioxan-6-yl)carboxamide |
| 122 | | {[4-(2-cyano(4-pyridyloxy))-2-nitrophenyl]amino}-N-(2,2,3,3-tetrafluorobenzo[e]1,4-dioxan-6-yl)carboxamide |

TABLE 1-continued

Examples of preferred compounds of formula (I)

| | | |
|---|---|---|
| 123 | | {[4-(2-cyano(4-pyridyloxy))phenyl]amino}-N-(2,2,4,4-tetrafluorobenzo[3,4-e]1,3-dioxan-6-yl)carboxamide |
| 124 | | {[4-(2-cyano(4-pyridyloxy))-2-fluorophenyl]amino}-N-(2,2,4,4-tetrafluorobenzo[3,4-e]1,3-dioxan-6-yl)carboxamide |
| 125 | | {[3-chloro-4-(2-cyano(4-pyridyloxy))phenyl]amino}-N-(2,2,4,4-tetrafluorobenzo[3,4-e]1,3-dioxan-6-yl)carboxamide |
| 126 | | {[2-chloro-4-(2-cyano(4-pyridyloxy))phenyl]amino}-N-(2,2,4,4-tetrafluorobenzo[3,4-e]1,3-dioxan-6-yl)carboxamide |
| 127 | | {[4-(2-cyano(4-pyridyloxy))-3-fluorophenyl]amino}-N-(2,2,4,4-tetrafluorobenzo[3,4-e]1,3-dioxan-6-yl)carboxamide |
| 128 | | {[4-(2-cyano(4-pyridyloxy))-2-(trifluoromethyl)phenyl]amino}-N-(2,2,4,4-tetrafluorobenzo[3,4-e]1,3-dioxan-6-yl)carboxamide |

TABLE 1-continued

Examples of preferred compounds of formula (I)

| | | |
|---|---|---|
| 129 | [structure] | {[4-(2-cyano(4-pyridyloxy))-2,3-difluorophenyl]amino}-N-(2,2,4,4-tetrafluorobenzo[3,4-e]1,3-dioxan-6-yl)carboxamide |
| 130 | [structure] | {[4-(2-cyano(4-pyridyloxy))-2,5-difluorophenyl]amino}-N-(2,2,4,4-tetrafluorobenzo[3,4-e]1,3-dioxan-6-yl)carboxamide |
| 131 | [structure] | {[4-(2-cyano(4-pyridyloxy))-2,6-difluorophenyl]amino}-N-(2,2,4,4-tetrafluorobenzo[3,4-e]1,3-dioxan-6-yl)carboxamide |
| 132 | [structure] | {[4-(2-cyano(4-pyridyl)oxy)-3-methoxyphenyl]amino}-N-(2,2,4,4-tetrafluorobenzo[3,4-e]1,3-dioxan-6-yl)carboxamide |
| 133 | [structure] | {[3-bromo-4-(2-cyano(4-pyridyloxy))phenyl]amino}-N-(2,2,4,4-tetrafluorobenzo[3,4-e]1,3-dioxan-6-yl)carboxamide |
| 134 | [structure] | {[4-(2-cyano(4-pyridyloxy))-2-methylphenyl]amino}-N-(2,2,4,4-tetrafluorobenzo[3,4-e]1,3-dioxan-6-yl)carboxamide |

TABLE 1-continued

Examples of preferred compounds of formula (I)

| 135 | 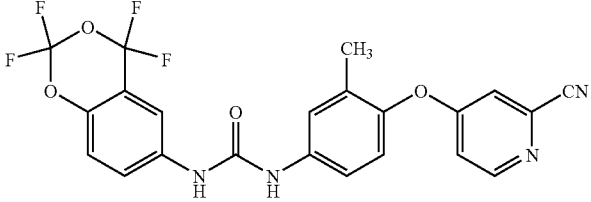 | {[4-(2-cyano(4-pyridyloxy))-3-methylphenyl]amino}-N-(2,2,4,4-tetrafluorobenzo[3,4-e]1,3-dioxan-6-yl)carboxamide |
| 136 | 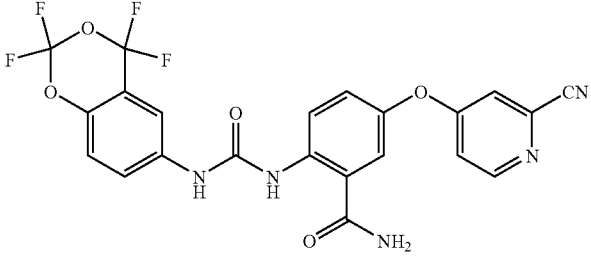 | 5-(2-cyano(4-pyridyl)oxy)-2-{[N-(2,2,4,4-tetrafluorobenzo[3,4-e]1,3-dioxan-6-yl)carbamoyl]amino}benzamide |
| 137 | 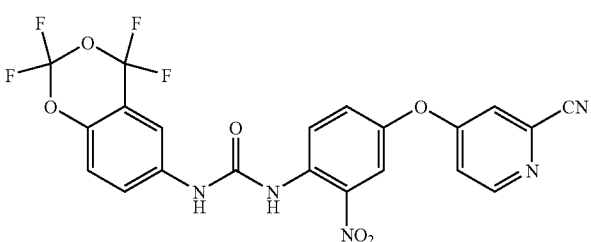 | {[4-(2-cyano(4-pyridyloxy))-2-nitrophenyl]amino}-N-(2,2,4,4-tetrafluorobenzo[3,4-e]1,3-dioxan-6-yl)carboxamide |
| 138 | 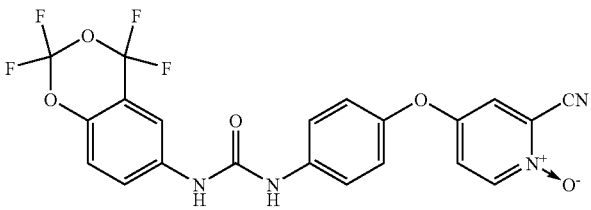 | {[4-(2-cyano-1-hydroxy(4-pyridyloxy))phenyl]amino}-N-(2,2,4,4-tetrafluorobenzo[3,4-e]1,3-dioxan-6-yl)carboxamide |
| 139 | 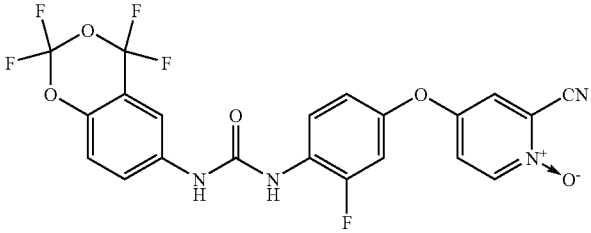 | {[4-(2-cyano-1-hydroxy(4-pyridyloxy))-2-fluorophenyl]amino}-N-(2,2,4,4-tetrafluorobenzo[3,4-e]1,3-dioxan-6-yl)carboxamide |
| 140 | 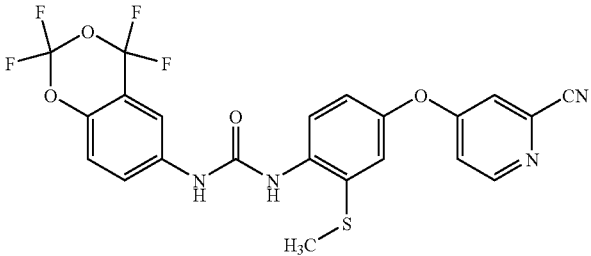 | {[4-(2-cyano(4-pyridyl)oxy)-2-methylthiophenyl]amino}-N-(2,2,4,4-tetrafluorobenzo[3,4-e]1,3-dioxan-6-yl)carboxamide |

TABLE 1-continued

Examples of preferred compounds of formula (I)

| | | |
|---|---|---|
| 141 | 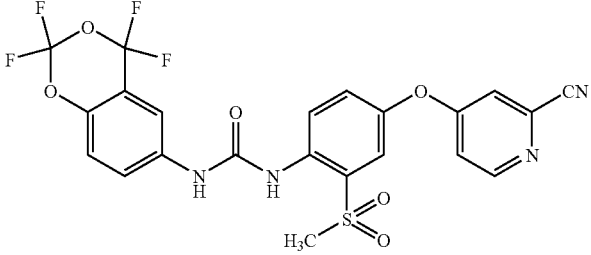 | {[4-(2-cyano(4-pyridyl)oxy)-2-(methylsulfonyl)phenyl]amino}-N-(2,2,4,4-tetrafluorobenzo[3,4-e]1,3-dioxan-6-yl)carboxamide |
| 142 | 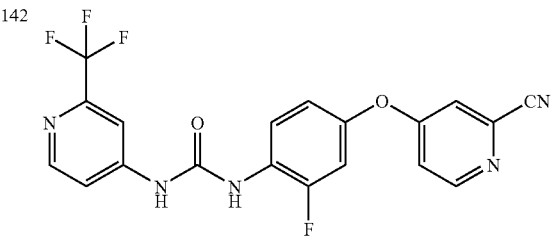 | {[4-(2-cyano(4-pyridyloxy))-2-fluorophenyl]amino}-N-[2-(trifluoromethyl)(4-pyridyl)]carboxamide |
| 143 | 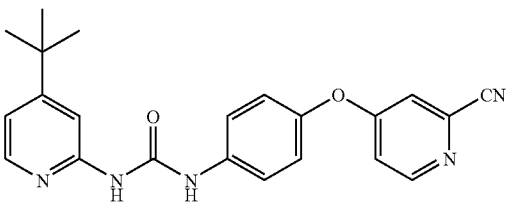 | N-[4-(tert-butyl)(2-pyridyl)]{[4-(2-cyano(4-pyridyloxy))phenyl]amino}carboxamide |
| 144 | 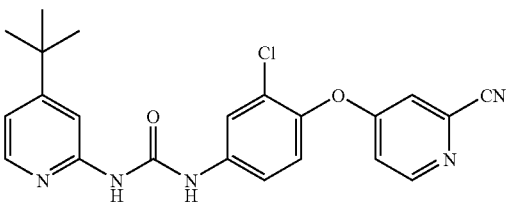 | N-[4-(tert-butyl)(2-pyridyl)]{[3-chloro-4-(2-cyano(4-pyridyloxy))phenyl]amino}carboxamide |
| 145 | 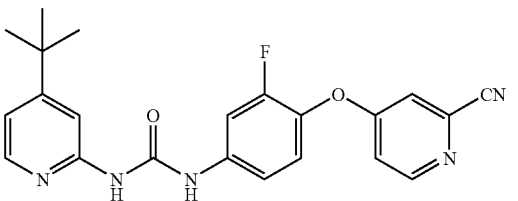 | N-[4-(tert-butyl)(2-pyridyl)]{[4-(2-cyano(4-pyridyloxy))-3-fluorophenyl]amino}carboxamide |
| 146 | 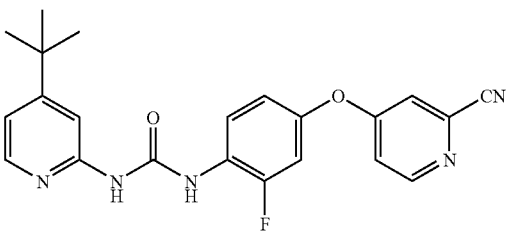 | N-[4-(tert-butyl)(2-pyridyl)]{[4-(2-cyano(4-pyridyloxy))-2-fluorophenyl]amino}carboxamide |

TABLE 1-continued

Examples of preferred compounds of formula (I)

| 147 | 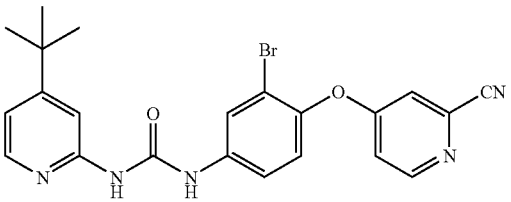 | N-[4-(tert-butyl)(2-pyridyl)]{[3-bromo-4-(2-cyano(4-pyridyloxy))phenyl]amino}carboxamide |
| 148 | 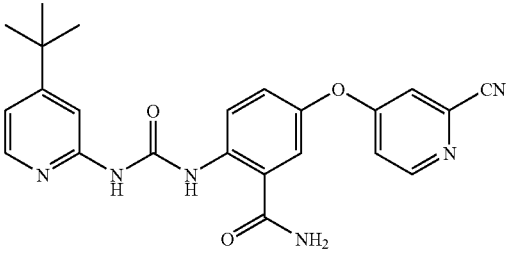 | 2-({N-[4-(tert-butyl)(2-pyridyl)]carbamoyl}amino)-5-(2-cyano(4-pyridyl)oxy)benzamide |
| 149 | 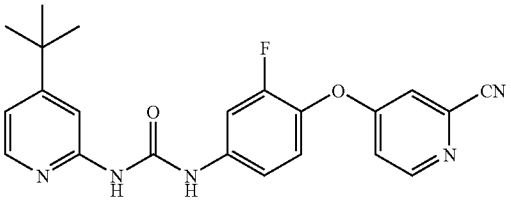 | N-[4-(tert-butyl)(2-pyridyl)]{[4-(2-cyano(4-pyridyloxy))-3-fluorophenyl]amino}carboxamide |
| 150 | 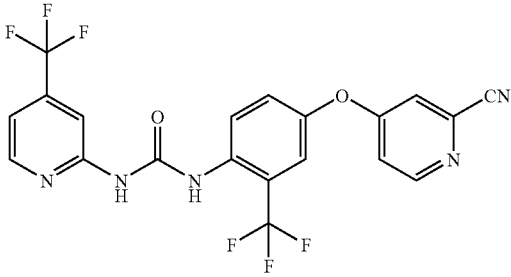 | {[4-(2-cyano(4-pyridyloxy))-2-(trifluoromethyl)phenyl]amino}-N-[4-(trifluoromethyl)(2-pyridyl)]carboxamide |
| 151 | 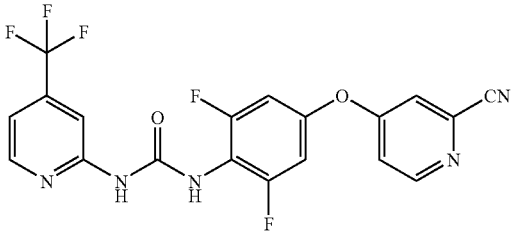 | {[4-(2-cyano(4-pyridyloxy))-2,6-difluorophenyl]amino}-N-[4-(trifluoromethyl)(2-pyridyl)]carboxamide |
| 152 | 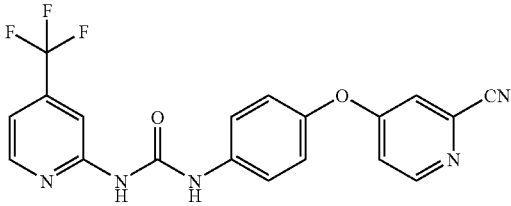 | {[4-(2-cyano(4-pyridyloxy))phenyl]amino}-N-[4-(trifluoromethyl)(2-pyridyl)]carboxamide |

TABLE 1-continued

Examples of preferred compounds of formula (I)

| | | |
|---|---|---|
| 153 | 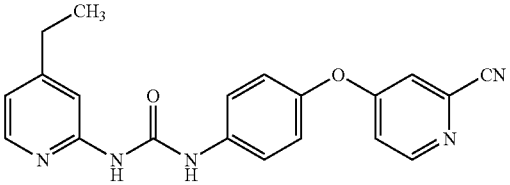 | {[4-(2-cyano(4-pyridyloxy))phenyl]amino}-N-(4-ethyl(2-pyridyl))carboxamide |
| 154 | 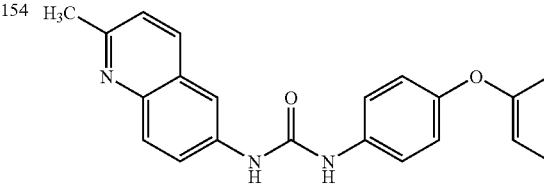 | {[4-(2-cyano(4-pyridyloxy))phenyl]amino}-N-(2-methyl(6-quinolyl))carboxamide |
| 155 | 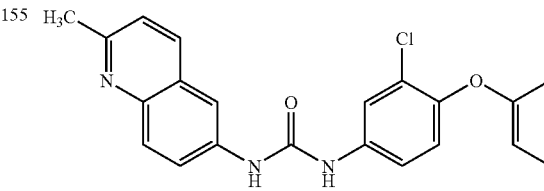 | {[3-chloro-4-(2-cyano(4-pyridyloxy))phenyl]amino}-N-(2-methyl(6-quinolyl))carboxamide |
| 156 | 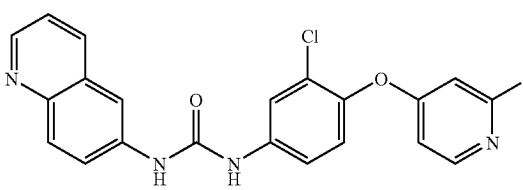 | {[3-chloro-4-(2-cyano(4-pyridyloxy))phenyl]amino}-N-(6-quinolyl)carboxamide |
| 157 | 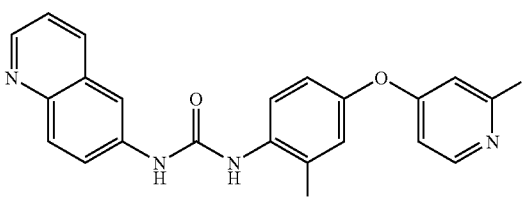 | {[2-chloro-4-(2-cyano(4-pyridyloxy))phenyl]amino}-N-(6-quinolyl)carboxamide |
| 158 | 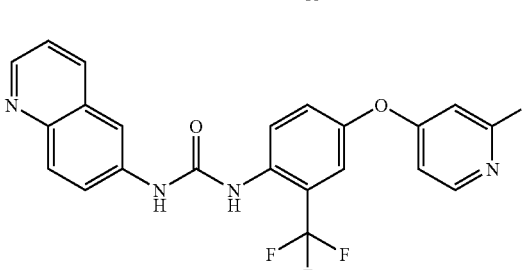 | {[4-(2-cyano(4-pyridyloxy))-2-(trifluoromethyl)phenyl]amino}-N-(6-quinolyl)carboxamide |
| 159 | 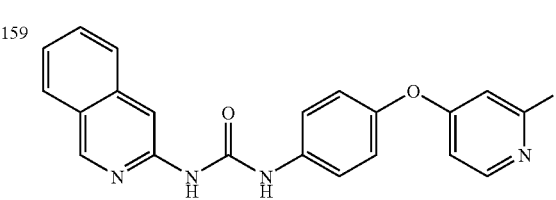 | {[4-(2-cyano(4-pyridyloxy))phenyl]amino}-N-(3-isoquinolyl)carboxamide |

TABLE 1-continued

Examples of preferred compounds of formula (I)

| 160 | {[4-(2-cyano(4-pyridyloxy))-2-fluorophenyl]amino}-N-(3-isoquinolyl)carboxamide |
| 161 | {[3-chloro-4-(2-cyano(4-pyridyloxy))phenyl]amino}-N-(3-isoquinolyl)carboxamide |
| 162 | {[4-(2-cyano(4-pyridyloxy))phenyl]amino}-N-(1-methyl(1H-indazol-5-yl))carboxamide |
| 163 | {[4-(2-cyano(4-pyridyloxy))-2-fluorophenyl]amino}-N-(1-methyl(1H-indazol-5-yl))carboxamide |
| 164 | {[2-chloro-4-(2-cyano(4-pyridyloxy))phenyl]amino}-N-(1-methyl(1H-indazol-5-yl))carboxamide |
| 165 | {[4-(2-cyano(4-pyridyloxy))-2-(trifluoromethyl)phenyl]amino}-N-(1-methyl(1H-indazol-5-yl))carboxamide |
| 166 | {[3-chloro-4-(2-cyano(4-pyridyloxy))phenyl]amino}-N-(1-methyl(1H-indazol-5-yl))carboxamide |

TABLE 1-continued

Examples of preferred compounds of formula (I)

| | | |
|---|---|---|
| 167 | [structure: 2-(trifluoromethyl)-1H-indazol-5-yl urea linked to 4-(2-cyano-4-pyridyloxy)phenyl] | {[4-(2-cyano(4-pyridyloxy))phenyl]amino}-N-[2-(trifluoromethyl)benzimidazol-5-yl]carboxamide |
| 168 | [structure: 2-(trifluoromethyl)-1H-indazol-5-yl urea linked to 3-chloro-4-(2-cyano-4-pyridyloxy)phenyl] | {[3-chloro-4-(2-cyano(4-pyridyloxy))phenyl]amino}-N-[2-(trifluoromethyl)benzimidazol-5-yl]carboxamide |
| 169 | [structure: benzothiazol-5-yl urea linked to 4-(2-cyano-4-pyridyloxy)-2-nitrophenyl] | N-benzothiazol-5-yl{[4-(2-cyano(4-pyridyloxy))-2-nitrophenyl]amino}carboxamide |
| 170 | [structure: 2-methylbenzothiazol-5-yl urea linked to 4-(2-cyano-4-pyridyloxy)-3-methylphenyl] | {[4-(2-cyano(4-pyridyloxy))-3-methylphenyl]amino}-N-(2-methylbenzothiazol-5-yl)carboxamide |

TABLE 2

Characterization of preferred compounds of formula (I)

| Entry | mp (° C.) | TLC $R_f$ | TLC Conditions | HPLC Ret. Time (min) | HPLC-MS (M$^+$ + 1) |
|---|---|---|---|---|---|
| 104 | | 0.41 | 50% ETOAC/HEX | 3.99 | 405 |
| 105 | | 0.50 | 50% EtOAc/hex | 3.55 | 389 |
| 106 | | 0.26 | 50% ETOAC/HEX | 3.44 | 419 |
| 107 | | 0.43 | | 3.51 | 399 |
| 108 | | | | 3.28 | 411 |
| 109 | 199-200 | 0.32 | 50% ETOAC/HEX | 3.84 | 411 |
| 110 | | 0.62 | 60% EtOAc/hex | 3.49 | 445 |
| 111 | 195-196 | 0.15 | 5% EtOAc/95% CH2Cl2 | | 429 |
| 112 | | 0.24 | 50% EtOAc/hex | 4.02 | 445 |
| 113 | 193.5-194.5 | 0.75 | 100% EtOAc | 3.45 | 429 |
| 114 | | | | 3.84 | 529 |
| 115 | | 0.19 | 50% ETOAC/HEX | 4.24 | 495 |
| 116 | | 0.30 | 50% ETOAC/HEX | 3.80 | 479 |
| 117 | | 0.28 | 50% EtOAc/hex | 3.93 | 497 |
| 118 | | 0.31 | 50% EtOAc/hex | 4.26 | 497 |
| 119 | | 0.11 | 50% EtOAc/hex | 4.25 | 495 |
| 120 | | 0.36 | 50% EtOAc/hex | | 475.5 |

TABLE 2-continued

Characterization of preferred compounds of formula (I)

| Entry | mp (° C.) | TLC $R_f$ | TLC Conditions | HPLC Ret. Time (min) | HPLC-MS (M⁺ + 1) |
|---|---|---|---|---|---|
| 121 | | 0.35 | 50% EtOAc/hex | | 475.4 |
| 122 | | 0.60 | 50% EtOAc/hex | | 506.1 |
| 123 | | 0.29 | 75% EtOAc/hex | | 461 |
| 124 | 169-171 | 0.38 | 50% EtOAc/hex | | 479 |
| 125 | | 0.38 | 67% EtOAc/hex | 4.20 | 495 |
| 126 | | 0.58 | 50% ETOAc/hex | 4.19 | 495 |
| 127 | 196-199.5 | 0.71 | 100% EtOAc | 4.11 | 479 |
| 128 | 220-221 | 0.33 | 35% EtOAc/hex | 3.82 | 529 |
| 129 | 181-182 | 0.29 | 35% EtOAc/hex | 4.14 | 497 |
| 130 | | 0.48 | 50% EtOAc/hex | 4.21 | 497 |
| 131 | | 0.56 | 50% EtOAc/hex | 3.90 | 497 |
| 132 | | 0.44 | 67% EtOAc/hex | 4.03 | 491 |
| 133 | | 0.26 | 50% EtOAc/hex | 3.83 | 539 |
| 134 | | 0.38 | 50% EtOAc/hex | | 475 |
| 135 | | 0.38 | 50% EtOAc/hex | | 475 |
| 136 | | 0.14 | 50% EtOAc/hex | 3.92 | 504 |
| 137 | | 0.65 | 50% EtOAc/hex | | 506.1 |
| 138 | | 0.30 | 100% ETOAC | 3.19 | 477 |
| 139 | | 0.18 | 80% ETOAC/HEX | 3.66 | 495 |
| 140 | 183-185 | 0.22 | 40% EtOAC/HEX | 3.72 | 507 |
| 141 | 229-230 | 0.20 | 40% EtOAC/HEX | 4.02 | 539 |
| 142 | 192-193 | 0.33 | 50% ETOAC/HEX | 3.54 | 418 |
| 143 | 216-217 | 0.34 | 40% ETOAC/HEX | 2.90 | 388 |
| 144 | | 0.65 | 50% EtOAc/hex | 3.58 | 422 |
| 145 | | 0.40 | 40% ETOAC/60% HEXANE | 2.94 | 406 |
| 146 | | 0.48 | 50% ETOAc/hex | 3.09 | 406 |
| 147 | | 0.88 | 50% EtOAc/hex | 3.11 | 467 |
| 148 | | 0.56 | 100% EtOAc | 2.83 | 431 |
| 149 | | 0.88 | 100% EtOAc | 3.32 | 418 |
| 150 | 209-210.5 | 0.43 | 35% EtOAc/hex | 3.61 | 468 |
| 151 | | 0.40 | 50% EtOAc/hex | 3.64 | 436 |
| 152 | 202-202 | 0.16 | 30% ETOAC/HEX | 3.72 | 400 |
| 153 | 209-210 | 0.39 | 50% ETOAC/HEX | 2.93 | 360 |
| 154 | 245.5 | 0.50 | 5% MeOH/95% EtOAc | 2.65 | 396 |
| 155 | | 0.10 | 100% EtOAc | 2.29 | 430 |
| 156 | | 0.47 | 8% MeOH/CH2Cl2 | 2.82 | 416 |
| 157 | | 0.47 | 60% EtOAc/hex | 2.79 | 416 |
| 158 | | | | 2.74 | 450 |
| 159 | 208-212 | 0.32 | 50% EtOAc/hex | 2.99 | 382 |
| 160 | 218-220 | | | 2.40* | 400 |
| 161 | | 0.24 | 50% EtOAc/hex | 3.33 | 416 |
| 162 | | 0.22 | 75% EtOAc/hex | | 385 |
| 163 | | 0.63 | 100% EtOAc | | 403 |
| 164 | | 0.33 | 60% EtOAc/hex | 2.82 | 419 |
| 165 | 239-240 | | | 3.07 | 455 |
| 166 | | 0.30 | 67% EtOAc/hex | 3.40 | 419 |
| 167 | 200-201 | 0.26 | 60% EtOAc/hex | 3.24 | 439 |
| 168 | | 0.36 | 100% EtOAc | 3.45 | 473 |
| 169 | | 0.36 | 50% EtOAc/hex | | |
| 170 | | 0.12 | 50% EtOAc/hex | | 416.1 |

*The following are the LCMS conditions: HPLC - electrospray mass spectra (HPLC ES-MS) were obtained using a Gilson HPLC system equipped with two Gilson 306 pumps, a Gilson 215 Autosampler, a Gilson diode array detector, a YMC Pro C-18 column (2 × 23 mm, 120 A), and a Micromass LCZ single quadrupole mass spectrometer with z-spray electrospray ionization. Spectra were scanned from 120-1000 amu over 2 seconds. ELSD (Evaporative Light Scattering Detector) data was also acquired as an analog channel. Gradient elution was used with Buffer A as 2% acetonitrile in water with 0.02% TFA and Buffer B as 2% water in Acetonitrile with 0.02% TFA at 1.5 mL/min. Samples were eluted as follows: 90% A for 0.5 min ramped to 95% B over 3.5 min and held at 95% B for 0.5 min and then the column is brought back to initial conditions over 0.1 min. Total run time is 4.8 min.
**comm refers to commercially available materials.

Other compounds of Formula (I) may be prepared using the methods described herein or other methods known in the art, and using the appropriate starting materials and/or intermediates that would be readily recognized by those skilled in the art.

Biological Tests

In-Vitro p38 Kinase Assay No. 1

Purified and His-tagged p38 α2 (expressed in *E. Coli*) was activated in vitro by MMK-6 to a high specific activity. Using a microtiter format, all reactions were conducted in 100 μL volumes with reagents diluted to yield 0.05 μg/well of activated p38 α2 and 10 μg/well of myelin basic protein in assay buffer (25 mM HEPES 7.4, 20 mM $MgCl_2$, 150 mM NaCl). Test compounds (5 μL of a 10% DMSO solution in water) were prepared and diluted into the assay to cover a final concentration range from 5 nM to 2.5 μM. The kinase assay was initiated by addition of 25 μL of an ATP cocktail to give a final concentration of 10 μM cold ATP and 0.2 μCi [γ-$^{33}$P] ATP per well (200-400 dpm/pmol of ATP). The plate was incubated at 32° C. for 35 min., and the reaction quenched with 7 μL of a 1 N aq HCl solution. The samples were harvested onto a P30 Filtermat (Wallac, Inc.) using a TomTec 1295 Harvester (Wallac, Inc.), and counted in a LKB 1205 Betaplate Liquid Scintillation Counter (Wallac, Inc.). Negative controls included substrate plus ATP alone. SW1353 cellular assay: SW1353 cells (human chondro-sarcoma) are seeded (1000 cells/100 μL DMEM 10% FCS/well) into 96-well plates and incubated overnight. After medium replacement, cells are exposed to test compounds for 1 h at 37° C., at which time human IL-1 (1 ng/mL, Endogen, Woburn, Wash.) and recombinant human TNFα (10 ng/mL) are added. Cultures are incubated for 48 h at 37° C., then supernatant IL-6 values are determined by ELISA. The compound of this invention shows significant inhibition of p38 kinase.

Murine VEGFR-2 Biochemical Assay

This assay was performed in 96-well opaque plates (Costar 3915) in the TR-FRET format. Reaction conditions are as follows: 10 μM ATP, 25 nM poly GT-biotin, 2 nM Eu-labelled phospho-Tyr Ab, 10 nM APC, 7 nM Flk-1 (kinase domain), 1% DMSO, 50 mM HEPES pH 7.5, 10 mM $MgCl_2$, 0.1 mM EDTA, 0.015% BRIJ, 0.1 mg/mL BSA, 0.1% mercapto-ethanol). Reaction is initiated upon addition of enzyme. Final reaction volume in each well is 100 μL. Plates are read at both 615 and 665 nM on a Perkin Elmer Victor V Multilabel counter at about 1.5-2.0 hours after reaction initiation. Signal is calculated as a ratio: (665 nm /615 nm)*10000 for each well.

The compound of this invention shows significant inhibition of VEGFR2 kinase.

Murine PDGFR FRET Biochemical Assay

This assay was formatted in a 96-well black plate (Costar 3915). The following reagents are used: Europium-labeled anti-phosphotyrosine antibody pY20 (Perand streptavidin-APC; poly GT-biotin from, and mouse PDGFR. The reaction conditions are as follows: 1 nM mouse PDGFR is combined with 20 μM ATP, 7 nM poly GT-biotin, 1 nM pY20 antibody, 5 nM streptavidin-APC, and 1% DMSO in assay buffer (50 mM HEPES pH 7.5, 10 mM $MgCl_2$, 0.1 mM EDTA, 0.015% BRIJ 35, 0.1 mg/mL BSA, 0.1% mercaptoethanol). Reaction is initiated upon addition of enzyme. Final reaction volume in each well is 100 μL. After 90 minutes, the reaction is stopped by addition of 10 μL/well of 5 μM staurosporine. Plates are read at both 615 and 665 nm on a Perkin Elmer VictorV Multilabel counter at about 1 hour after the reaction is stopped. Signal is calculated as a ratio: (665 nm/615 nm)*10000 for each well.

The compound of this invention shows significant inhibition of PDGFR kinase.

For $IC_{50}$ generation for both PDGFR and Flk-1, compounds were added prior to the enzyme initiation. A 50-fold stock plate was made with compounds serially diluted 1:3 in a 50% DMSO/50% dH2O solution. A 2 μL addition of the stock to the assay gave final compound concentrations ranging from 10 μM-4.56 nM in 1% DMSO. The data were expressed as percent inhibition: % inhibition=100-((Signal with inhibitor-background)/(Signal without inhibitor-background))*100 pPDGFR-b sandwich ELISA in AoSMC cells

100 K P3-P6 Aortic SMC were plated in each well of 12-well cluster in 1000 μL volume/well of SGM-2 using standard cell culture techniques. Next day, cells were rinsed with 1000 μL D-PBS once, then serum starved in 500 μL SBM (smooth muscle cell basal media) with 0.1% BSA overnight. Compounds were diluted at a dose range from (10 μM to 1 nM in 10-fold dilution steps in DMSO, final DMSO concentration 0.1%). Remove old media by inversion into the sink quickly then add 100 μl of each dilution to corresponding well of cells for 1 hr at 37° C. Cells were then stimulated with 10 ng/mL PDGF BB ligand for 7 minutes at 37° C. The media is decanted and 150 μL of isotonic lysis buffer with protease inhibitor tablet (Complete; EDTA-free) and 0.2 mM Na vanadate is added. Cells are lysed for 15 min at 4° C. on shaker in cold room. Lysates are put in eppendorf tubes to which 15 μL of agarose-conjugated anti-PDGFR-b antibody is added and incubated at 4° C. overnight. Next day, beads are rinsed in 50-volumes of PBS three times and boiled in 1× LDS sample buffer for 5 minutes. Samples were run on 3-8% gradient Tris-Acetate gels and transferred onto Nitrocellulose. Membranes were blocked in 1% BSA/TBS-T for 1 hr. before incubation in anti-phospho-PDGFR-b (Tyr-857) antibody in blocking buffer (1:1000 dilution) for 1 hour. After three washes in TBS-T, membranes were incubated in Goat anti-rabbit HRP IgG (1:25000 dilution) for 1 hr. Three more washes followed before addition of ECL substrate. Membranes were exposed to Hyperfilm-ECL. Subsequently, membranes were stripped and reprobed with anti-PDGFR-b antibody for total PDGFR-b.

c-Raf (Raf-1) Biochemical Assay

Purification of Proteins Used in the Assay

The c-Raf biochemical assay was performed with a c-Raf enzyme that was activated (phosphorylated) by Lck kinase. Lck-activated c-Raf (Lck/c-Raf) was produced in Sf9 insect cells by co-infecting cells with baculoviruses expressing, under the control of the polyhedrin promoter, GST-c-Raf (from amino acid 302 to amino acid 648) and Lck (full-length). Both baculoviruses were used at the multiplicity of infection of 2.5 and the cells were harvested 48 hours post infection.

MEK-1 protein was produced in Sf9 insect cells by infecting cells with the baculovirus expressing GST-MEK-1 (full-length) fusion protein at the multiplicity of infection of 5 and harvesting the cells 48 hours post infection. Similar purification procedure was used for GST-c-Raf 302-648 and GST-MEK-1.

Transfected cells were suspended at 100 mg of wet cell biomass per mL in a buffer containing 10 mM sodium phosphate, 140 mM sodium chloride pH 7.3, 0.5% Triton X-100 and the protease inhibitor cocktail. The cells were disrupted with Polytron homogenizer and centrifuged 30,000 g for 30 minutes. The 30,000 g supernatant was applied onto GSH-Sepharose. The resin was washed with a buffer containing 50 mM Tris, pH 8.0, 150 mM NaCl and 0.01% Triton X-100. The GST-tagged proteins were eluted with a solution containing 100 mM Glutathione, 50 mM Tris, pH 8.0, 150 mM NaCl and 0.01% Triton X-100. The purified proteins were dialyzed into a buffer containing 20 mM Tris, pH 7.5, 150 mM NaCl and 20% Glycerol.

Biochemical Assay Protocol and Results

The compounds were serially diluted in DMSO using three-fold dilutions to stock concentrations ranging typically from 50 μM to 20 nM (final concentrations in the assay range from 1 μM to 0.4 nM). The c-Raf biochemical assay was performed as a radioactive filtermat assay in 96-well Costar polypropylene plates (Costar 3365). The plates were loaded with 75 μL solution containing 50 mM HEPES pH 7.5, 70 mM NaCl, 80 ng of Lck/c-Raf and 1 μg MEK-1. Subsequently, 2 μL of the serially diluted individual compounds were added to the reaction, prior to the addition of ATP. The reaction was initiated with 25 μL ATP solution containing 5 μM ATP and 0.3 μCi [33P]-ATP. The plates were sealed and incubated at 32° C. for 1 hour. The reaction was quenched with the addition of 50 μl of 4% Phosphoric Acid and harvested onto P30 filtermats (PerkinElmer) using a Wallac Tomtec Harvester. Filtermats were washed with 1% Phosphoric Acid first and deionized $H_2O$ second. The filters were dried in a microwave, soaked in scintillation fluid and read in a Wallac 1205 Betaplate Counter (Wallac Inc., Atlanta, Ga., U.S.A.). The results were expressed as percent inhibition.

% Inhibition=$[100-(T_{ib}/T_i)] \times 100$ where $T_{ib}$=(counts per minute with inhibitor)−(background)
$T_i$=(counts per minute without inhibitor)−(background)

Assay Results

The biological inhibition activity of the compounds of the present invention was tested in various inhibition assays such as those described above. The compounds exhibited a range of inhibitory activity described below:
a) h-Flt4 v2 assay $IC_{50}$ (nM) values for the preferred compounds of the present invention range from 0.66 to 3000,
b) m-Flt4 assay $IC_{50}$ (nM) values for the preferred compounds of the present invention range from 11.4 to >10,000,
c) Flk1 FRET assay $IC_{50}$ (nM) values for the preferred compounds of the present invention range from 6.97 to 186,
d) c-RAF-1 assay $IC_{50}$ (nM) values for the preferred compounds of the present invention range from 7.86 to >1600,
e) cRaf v2 assay $IC_{50}$ (nM) values for the preferred compounds of the present invention range from 7.9 to 1000.

Overall, compounds of the present invention provide a unique combination of angiogenesis and tumor cell proliferation, through an improved inhibition profile against several key kinase targets such as raf, p38, PDGFR, VEGFR3 and VEGFR2, which are all molecular targets of interest for the treatment of diseases, including cancer.

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

What is claimed is:
1. A compound of Formula (I)

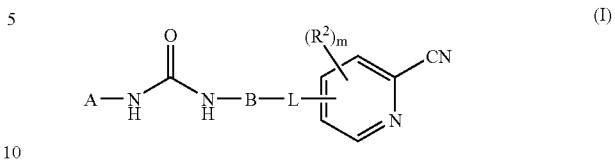

or a pharmaceutically acceptable acid salt or basic salt thereof,
wherein A is unsubstituted or substituted 2H,3H-benzo[e]1,4-dioxan-6-yl, 2H,4H-benzo[e]1,3-dioxan-6-yl, or 2H,4H-benzo[e]1,3-dioxan-8-yl wherein the substituents of the substituted 2H,3H-benzo[e]1,4-dioxan-6-yl, 2H,4H-benzo[e]1,3-dioxan-6-yl, or 2H,4H-benzo[e]1,3-dioxan-8-yl are substituted by $(R^3)_n$ wherein n is an integer 0, 1, 2, 3, 4, 5, or 6 and
each $R^3$ is independently
halogen,
$R^4$,
$OR^4$,
$S(O)R^4$,
$C(O)R^4$,
$C(O)NR^4R^5$,
oxo,
cyano or
$NO_2$; and
$R^4$ and $R^5$ are independently hydrogen, $C_{1-6}$alkyl, or up to per-halogenated $C_{1-6}$alkyl,
B is selected from the group consisting of

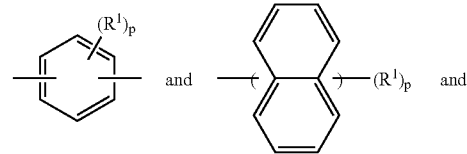

p is an integer 0, 1, 2, 3, or 4, each $R^1$ is independently
halogen,
$C_{1-5}$haloalkyl,
$NO_2$;
$C(O)NR^4R^5$
$C_{1-6}$alkyl,
$C_{1-6}$dialkylamine,
$C_{1-3}$alkylamine,
CN,
amino,
hydroxyl or $C_{1-3}$alkoxy
$SCH_3$,
methylsulfonyl,
$R^4$ and $R^5$ are independently hydrogen, $C_{1-6}$alkyl, or up to per-halogenated $C_{1-6}$alkyl,
L is O or S,
m is an integer 0, 1, 2, or 3, and
each $R^2$ is independently $C_{1-5}$alkyl, $C_{1-5}$haloalkyl, $C_{1-3}$alkoxy, N-oxo or N-hydroxy.

2. A compound of claim 1, wherein L is oxygen.

3. A compound of claim 1, wherein $R^1$ is fluorine, chlorine, bromine, methyl, $NO_2$, C(=O)$NH_2$, methoxy, trifluoromethyl.

4. A compound of claim 1, wherein $R^2$ is methyl, ethyl, propyl, or oxygen.

5. A compound of claim 1, wherein $R^3$ is trifluoromethyl, methyl, ethyl, propyl, butyl, isopropyl, tert-butyl, chlorine, fluorine, bromine, cyano, methoxy, acetyl, triflurometyl sulfonyl, trifuoromethoxy, or trifluoromethylthio.

6. A compound which is
{[4-(2-cyano(4-pyridyloxy))-2-(trifluoromethyl)phenyl]amino}-N-(2,2,3,3-tetrafluorobenzo[e]1,4-dioxan-6-yl)carboxamide;
{[2-chloro-4-(2-cyano(4-pyridyloxy))phenyl]amino}-N-(2,2,3,3-tetrafluorobenzo[e]1,4-dioxan-6-yl)carboxamide;
{[4-(2-cyano(4-pyridyloxy))-2-fluorophenyl]amino}-N-(2,2,3,3-tetra-fluorobenzo[e]1,4-dioxan-6-yl)carboxamide;
{[4-(2-cyano(4-pyridyloxy))-2,6-difluorophenyl]amino}-N-(2,2,3,3-tetrafluorobenzo[e]1,4-dioxan-6-yl)carboxamide;
{[4-(2-cyano(4-pyridyloxy))-2,5-difluorophenyl]amino}-N-(2,2,3,3-t-etrafluorobenzo[e]1,4-dioxan-6-yl)carboxamide;
{[3-chloro-4-(2-cyano(4-pyridyloxy))phenyl]amino}-N-(2,2,3,3-tetrafluorobenzo[e]1,4-dioxan-6-yl)carboxamide;
{[4-(2-cyano(4-pyridyloxy))-2-methyl phenyl]amino}-N-(2,2,3,3-tetr-afluorobenzo[e]1,4-dioxan-6-yl)carboxamide;
{[4-(2-cyano(4-pyridyloxy))-3- methyiphenyl]amino}-N-(2,2,3,3-tetrafluorobenzo[e]1,4-dioxan-6-yl)carboxamide;
{[4-(2-cyano(4-pyridyloxy))-2-nitrophenyl]amino}-N-(2,2,3,3-tetrafluo-robenzo[e]1,4-dioxan-6-yl)carboxamide;
{[4-(2-cyano(4-pyridyloxy))phenyl]amino}-N-(2,2,4,4-tetrafluorobenzo[3,4-e]1,3-dioxan-6-yl)carboxamide;
{[4-(2-cyano(4-pyridyloxy))-2-fluorophenyl]amino}-N-(2,2,4,4-tetrafluorob-enzo[3,4-e]1,3-dioxan-6-yl)carboxamide;
{[3-chloro-4-(2-cyano(4-pyridyloxy))phenyl]amino}-N-(2,2,4,4-tetrafluorobenzo[3,4-e]1,3-dioxan-6-yl)carboxamide;
{[2-chloro-4-(2-cyano(4-pyridyloxy))phenyl]amino}-N-(2,2,4,4-tetraflu-orobenzo[3,4-e]1,3-dioxan-6-yl)carboxamide;
{[4-(2-cyano(4-pyridyloxy))-3-fluorophenyl]amino}-N-(2,2,4,4-tetrafluorobenzo[3,4-e]1,3-dioxan-6-yl)carboxamide;
{[4-(2-cyano(4-pyridyloxy))-2-(trifluoromethyl)phenyl]amino}-N-(2,2,4,4-tetrafluorobenzo[3,4-e]1,3-dioxan-6-yl)carboxamide;
{[4-(2-cyano(4-pyridyloxy))-2 ,3-difluorophenyl]amino}-N-(2,2,4,4-tetrafluorobenzo[3,4-e]1,3-dioxan-6-yl)carboxamide;
{[4-(2-cyano(4-pyridyloxy))-2,- 5-difluorophenyl]amino}-N-(2,2 14,4-tetrafluorobenzo[3,4-e]1,3-dioxan-6-yl)carboxamide;
{[4-(2-cyano(4-pyridyloxy))-2,6-difluorophenyl]amino}-N-(2,2,4,4-tetrafluorobenzo[3,4-e]1,3-dioxan-6-yl)carboxamide;
{[4-(2-cyano(4-pyridyl)oxy)-3-methoxyphenyl]amino}-N-(2,2,4,4-tetrafluoro-benzo[3,4-e]1,3-dioxan-6-yl)carboxamide;
{[3-bromo-4-(2-cyano(4-pyridyloxy))phenyl]amino}-N-(2,2,4,4-tetrafluorobenzo[3,4-e]1,3-dioxan-6-yl)carboxamide;
{[4-(2-cyano(4-pyridyloxy))-2-methylphenyl]amino}-N-(2,2,4,4-tetraflu-orobenzo[3,4-e]1,3-dioxan-6-yl)carboxamide;
{[4-(2-cyano(4-pyridyloxy))-3-methylphenyl]amino}-N-(2,2,4,4-tetrafluorobenzo[3,4-e]1,3-dioxan-6-yl)carboxamide;
5-(2-cyano(4-pyridyl )oxy)-2-{[N-(2,2,4,4-tetrafluorobenzo[3,4-e]1,3-dioxan-6-yl )carbamoyl]amino}benzamide
{[4-(2-cyano(4-pyridyloxy))-2-nitrophenyl]amino}-N-(2,2,4,4-tetrafluorobenzo[3,4-e]1,3-dioxan-6-yl)carboxamide;
{[4-(2-cyano-1 -hydroxy(4-pyridyloxy))phenyl]amino}-N-(2,2,4,4-tetrafluorobenzo[3,4-e]1,3-dioxan-6-yl)carboxamide;
{[4-(2-cyano-1 -hydroxy(4-pyridyloxy))-2-fluorophenyl]amino}-N-(2,2,4,4-tetrafluorobenzo[3,4-e]1,3-dioxan-6-yl)carboxamide;
{[4-(2-cyano(4-pyridyl)oxy)-2-methylthiophenyl]amino}-N-(2,2,4,4-tetrafluorobenzo[3,4-e]1,3-dioxan-6-yl)carboxamide;
{[4-(2-cyano(4-pyridyl)oxy)-2-(methylsulfonyl)phenyl]amino}-N-(2,2,4,4-tetrafluorobenzo[3,4-e]1 ,3-dioxan-6-yl)carboxamide;

or a pharmaceutically acceptable salt thereof or an isolated stereolsomer thereof.

7. A compound of claim 1, which is a pharmaceutically acceptable basic salt of an organic acid of formula (I).

8. A compound of claim 1, which is a pharmaceutically acceptable acid salt of a compound of formula (I) which is a salt of an organic base or an inorganic base.

9. A compound of Formula Y

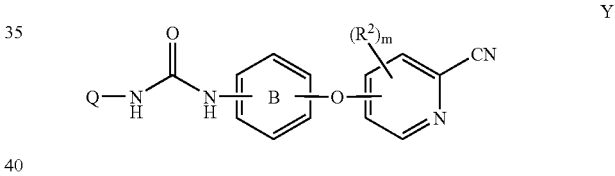

or a pharmaceutically acceptable salt thereof,
wherein Q is 2H,3H-benzo[e]1,4-dioxan-6-yl, 2H,4H-benzo[e]1,3-dioxan-6-yl, or 2H,4H-benzo[e]1,3-dioxan-8-yl, substituted with at least one halogen, each $R^2$ is independently $C_{1-5}$alkyl, $C_{1-5}$haloakyl, $C_{1-3}$alkoxy, N-oxo or N-hydroxy; m is 0, 1, 2 or 3; and phenyl ring "B" is substituted by one or more fluorine atoms.

10. A compound of claim 9 wherein phenyl ring "B" is substituted by 2-4 fluorine atoms.

11. A compound of claim 9 wherein phenyl ring "B" is substituted by 2-4 fluorine atoms and Q is substituted by 2-4 fluorine atoms.

12. A compound of claim 9 wherein Q is 2,2,4,4-tetrafluorobenzo[3,4-e]1,3-dioxan-6-yl or 2,2,3,3-tetrafluorobenzo[e]1,4-dioxan-6-yl.

13. A compound of formula II below

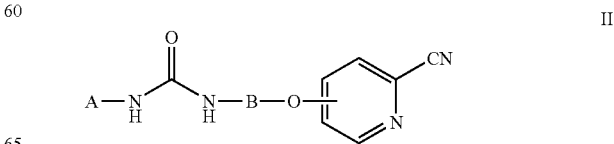

wherein B of formula II is

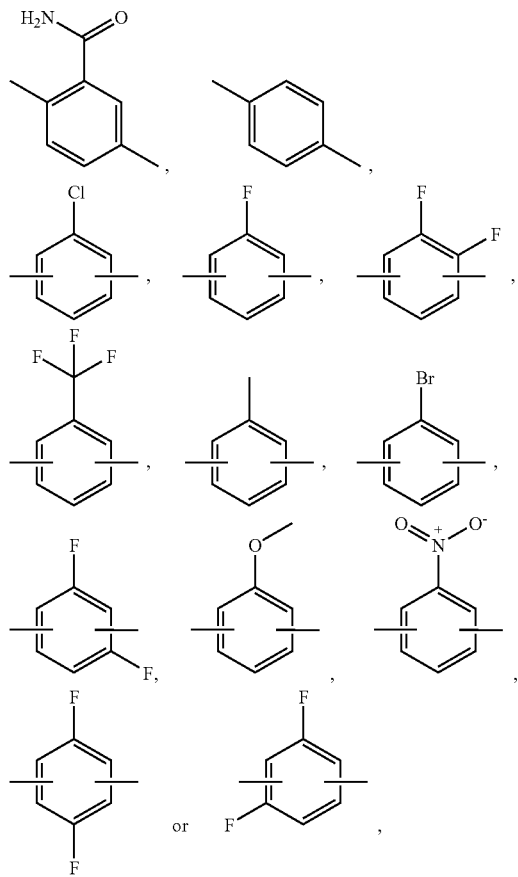

wherein the urea group, —NH—C(O)—NH—, and the bridging group, L, are not bound to contiguous ring carbons of B, but rather have 1 or 2 ring carbons separating them, A of the formula (II) is

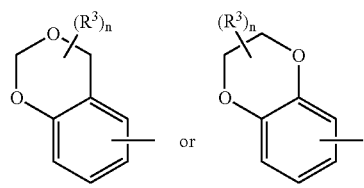

wherein the variable n is 0,1,2,3, or 4, and R³ is trifluoromethyl, methyl, ethyl, propyl, butyl, isopropyl, tert-butyl, chlorine, fluorine, bromine, cyano, methoxy, acetyl, trifluoromethanesulfonyl, trifluoromethoxy, or trifluoromethylthio.

14. A compound of claim 13 wherein each R³ substitutent is fluorine.

15. A compound of claim 13 wherein A of formula II is

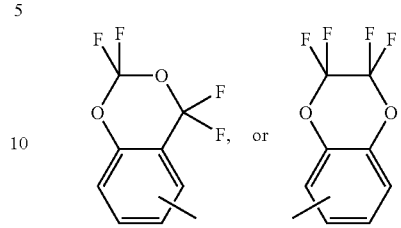

and B of the formula II is phenylene, fluoro substituted phenylene or difluoro substituted phenylene.

16. A compound of formulae:

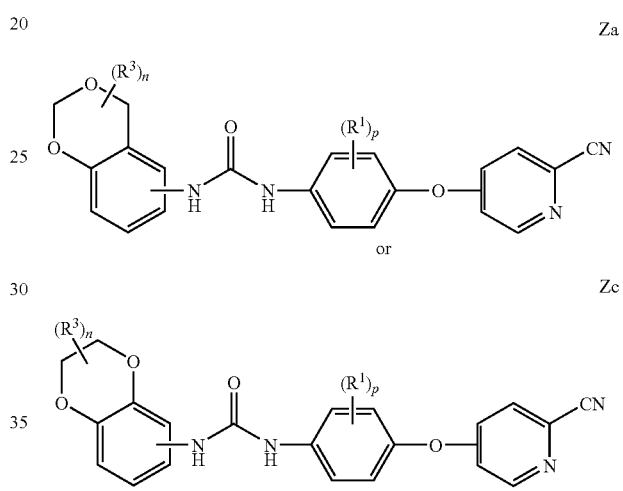

or a pharmaceutically acceptable salt thereof, or the nitrogen atom in the pyridine group is in the oxide form,
wherein
each R¹ is independently halogen or trifluoromethyl and each R³ is independently halogen, R⁴, OR⁴, S(O)R⁴, C(O)R⁴, C(O)NR⁴R⁵, oxo
or cyano or nitro (NO₂),
the variable n is 0, 1, 2, 3 or 4 and
the variable p is 0, 1 or 2.

17. A compound as in claim 16 wherein R³ is fluoro, trifluoromethyl, methyl or t-butyl.

18. A pharmaceutical composition comprising a compound of claim 1, or a pharmaceutically acceptable salt thereof, and a physiologically acceptable carrier.

* * * * *